United States Patent [19]

Li et al.

[11] Patent Number: 5,512,294
[45] Date of Patent: Apr. 30, 1996

[54] TARGETED POLYMERIZED LIPOSOME CONTRAST AGENTS

[76] Inventors: King C. Li, 21 Ryan Ct., Stanford, Calif. 94305; Mark D. Bednarski, 816 Amber La., Los Altos, Calif. 94024; Richard W. Storrs, 2755 Rose Bud Ct., Union City, Calif. 94587; Henry Y. Li, 3350 W. Sunnyside Ave., Visalia, Calif. 93277; Francois D. Trooper, 1851 Magellan Dr., Oakland, Calif. 94611; Curtis K. H. Song, 548 E. Maude Ave., Sunnyvale, Calif. 94086; Dorothy A. Sipkins, 933 Addison St., Palo Alto, Calif. 94301; Jeremy K. Kuniyoshi, 22344 Carta Blanca St., Cupertino, Calif. 95014

[21] Appl. No.: 286,555

[22] Filed: Aug. 5, 1994

[51] Int. Cl.$^6$ .................................................. A61K 9/127
[52] U.S. Cl. ....................... 424/450; 424/1.21; 436/829
[58] Field of Search .................................. 424/450, 1.21; 436/829

[56] References Cited

U.S. PATENT DOCUMENTS

| | | | |
|---|---|---|---|
| 4,544,545 | 10/1985 | Ryan et al. | 424/1.1 |
| 4,938,947 | 7/1990 | Nicolau et al. | 424/1.1 |
| 5,017,359 | 5/1991 | Nicolau et al. | 423/1.1 |
| 5,077,057 | 12/1991 | Szoka, Jr. | 424/450 |
| 5,078,986 | 1/1992 | Bosworth et al. | 424/9 |
| 5,135,737 | 8/1992 | Keana | 424/9 |
| 5,158,760 | 10/1992 | Phillips et al. | 424/1.1 |
| 5,213,804 | 5/1993 | Martin et al. | 424/450 |
| 5,246,707 | 9/1993 | Haynes | 424/450 |
| 5,277,914 | 1/1994 | Szoka, Jr. | 424/450 |
| 5,366,881 | 11/1994 | Singth | 435/177 |
| 5,387,410 | 2/1995 | Bosworth | 424/9 |
| 5,395,619 | 3/1995 | Zalipsky | 424/450 |

FOREIGN PATENT DOCUMENTS

| | | |
|---|---|---|
| 0054384 | 3/1988 | Japan. |
| 9221017 | 11/1992 | WIPO. |

OTHER PUBLICATIONS

Purnima Pinnaduwage and Leaf Haung, "Stable Target-Sensitive Immunoliposomes", *Biochemistry* (1992), 31, 2850–2855.

Marja–Leena Laukkanen, Kaija Alfthan, and Kari Keinanen, "Functional Immunoliposomes Harboring a Biosynthetically Lipid–Tagged Single–Chain Antibody", *Biochemistry* (1994), 33, 11664–11670.

Unger, E. C., Shen, D. K., and Fritz, T. A., Status of Liposomes as MR Contrast Agents, JMRI, 3, 195–198, (1993).

Gore, J. C. and Smith, F. W., Special Issue: Contrast Agents, Magn. Reson. Img., 3, 1–97, (1985).

Hasso, A. N. and Stark, D. D., Special Issue: Contrast Agents, JMRI, 3, 137–310, (1993).

Wehrli, F. W., SMRM Workshop: Contrast Enhanced Magnetic Resonance, Magn. Reson. Med., 22, 177–378, (1991).

Reimer, P., Weissleder, R. Brady, T. J., Baldwin, B. H., Tennant, B. C., and Wittenberg, J., Experimental Hepatocellular Carcinoma: MR Receptor Imaging, Radiology, 180, 641–645 (1991).

Reimer, P., Weisslender, R., Lee, A. S., and Brady, T. J., Receptor Imaging: Application to MR Imaging of Liver Cancer, Radiology, 177, 729–734 (1990).

Reimer, P., Weissleder, R., Wittenberg, J., and Brady, T. J., Receptor–Directed Contrast Agents for MR Imaging: Preclinical Evaluation With Affinity Assays, Radiology, 182, 565–569 (1992).

Weissleder, R., Reimer, P., Lee, A. S., Wittenberg, J. and Brady T. J., MR Receptor Imaging: Ultrasmall Iron Oxide Particles Targeted to Asialoglycoprotein Receptors, AJR, 155, 1161–67, (1990).

Unger, E. C., Totty, W. G., Neufeld, D. M., Otsuka, F. L., Murphy, W. A., Welch, M. S., Connett, J. M., and Philpott, G. W., Magnetic Resonance Imaging Using Gadolinium labeled Monoclonal Antibody, Invest. Radiol., 20, 693–700. (1985).

Weissleder, R., Lee, A. S., Fischman, A. J., Reimer, P., Shen, T., Wilkinson, R., Callahan, R. J., and Brady, T. J., Polyclonal Human Immunoglobulin G Labeled with polymeric Iron Oxide: Antibody MR Imaging, Radiology, 181, 245–249, (1991).

*Primary Examiner*—Gollamudi S. Kishore
*Attorney, Agent, or Firm*—Speckman, Pauley & Fejer

[57] ABSTRACT

Polymerized liposome particles based upon lipids having a polymerizable functional group and a metal chelator to attach an imaging enhancement agent and lipids having an active targeting group to provide targeted polymerized liposome contrast agents. The polymerized imaging enhancement liposome particles interact with receptor targets holding the image enhancement agent to specific sites providing in vivo study by magnetic resonance, radioactive, x-ray or optical imaging of the expression of molecules in cells and tissues during disease and pathology.

14 Claims, 19 Drawing Sheets

TARGETED POLYMERIZED LIPOSOME CONTRAST AGENTS

BACKGROUND OF THE INVENTION

1. Field of the Invention

This invention relates to liposomes which may be linked to contrast ions for magnetic resonance imaging and radioisotope imaging or optical imaging by using chromophores inherent in the particle. These liposomes are polymerized for stability in vivo. The paramagnetic or radioactive polymerized liposomes may also be linked to antibodies and ligands for specific interaction with receptor targets holding the contrast agent to specific sites, providing in vivo study of the expression of molecules in or on the surface of cells and tissues during disease and pathology.

2. Description of Related Art

Liposomes have been used as carriers for administration of drugs and paramagnetic contrast agents. U.S. Pat. Nos. 5,077,057 and 5,277,914 teach preparation of liposome or lipidic particle suspensions having particles of a defined size, particularly lipids soluble in an aprotic solvent, for delivery of drugs having poor aqueous solubility. U.S. Pat. No. 4,544,545 teaches phospholipid liposomes having an outer layer including a modified cholesterol derivative to render the liposome more specific for a preselected organ. U.S. Pat. No. 5,213,804 teaches liposome compositions containing an entrapped agent, such as a drug, which are composed of vesicle-forming lipids and 1 to 20 mole percent of a vesicle-forming lipid derivitized with hydrophilic biocompatible polymer and sized to control its biodistribution and recirculatory half life. U.S. Pat. Nos. 5,246,707 teaches phospholipid coated microcrystalline particles of bio-active material to control the rate of release of entrapped water soluble biomolecules, such as proteins and polypeptides. U.S. Pat. No. 5,158,760 teaches liposome encapsulated radio-active labeled proteins, such as hemoglobin.

The use of magnetic resonance imaging contrast enhancement agents or radioactive isotopes in the body is practiced by a variety of methods. U.S. Pat. No. 5,135,737 teaches magnetic resonance imaging enhancement agents of paramagnetic metal ion chelates attached to polymers such as polyamine based molecules with antibodies attached for concentration at desired sites in the body. U.S. Pat. Nos. 4,938,947 and 5,017,359 teach an aerosol composition containing soluble fragments of bacterial wall or cell peptidoglycan which may be labeled with a paramagnetic element and encapsulated in liposomes which may be administered as an aerosol. U.S. Pat. No. 5,078,986 teaches magnetic resonance imaging agents of a chelate of a paramagnetic element carried by or within the external surface of a liposome and released at a desired organ or tissue site. PCT Publication Number WO 92/21017 teaches specific liposomes complexed with paramagnetic ions to prolong their blood pool half life and control magnetic resonance relaxivity. Liposomes as MR contrast agents has been reviewed by Unger, E. C., Shen, D. K., and Fritz, T. A., Status of Liposomes as MR Contrast Agents, JMRI, 3, 195–198, (1993).

The need for recirculation of paramagnetic contrast agents in the body, that is avoidance of rapid endocytosis by the reticuloendothelial system and avoidance of rapid filtration by the kidney, to provide sufficient concentration at a targeted site to afford necessary contrast has been recognized. The use of small molecules, such as gadolinium diethylenetriaminepentaacetic acid, is restricted due to rapid renal excretion while most liposomes, having diameters >800 nm, are quickly cleared by the reticuloendothelial system. Attempts to solve these problems have involved use of macromolecular materials, such as gadolinium diethylenetriaminepentaacetic acid derived polysaccharides, polypeptides, and proteins. These agents have not achieved the versatility in chemical modification to provide for both long recirculation times and active targeting.

Prior attempts to construct bifunctional, ligand-bearing magnetic resonance contrast agents have not been satisfactory due to insufficient sensitivity, poor target specificity and lack of characterization. Gore, J. C. and Smith, F. W., Special Issue: Contrast Agents, Magn. Reson. Img., 3, 1–97, (1985); Hasso, A. N. and Stark, D. D., Special Issue: Contrast Agents, JMRI, 3, 137–310, (1993); and Wehrli, F. W., SMRM Workshop: Contrast Enhanced Magnetic Resonance, Magn. Reson.. Med., 22, 177–378, (1991).

Receptor-directed contrast agents for MRI has been attempted, but the chemistry and characterization of the particle has been poorly defined and thus it has been difficult to achieve control over non-specific adhesion, blood pool half life and the versatility for both T1 and T2* imaging modes. In addition, no radioisotope imaging is possible using these iron-based agents which further limits their usefulness. Reimer, P., Weissleder, R., Brady, T. J., Baldwin, B. H., Tennant,, B. C., and Wittenberg, J., Experimental Hepatocellular Carcinoma: MR Receptor Imaging, Radiology, 180, 641–645 (1991), Reimer, P., Weisslender, R., Lee, A. S., and Brady, T. J., Receptor Imaging: Application to MR Imaging of Liver Cancer, Radiology, 177, 729–734 (1990), Reimer, P., Weissleder, R., Wittenberg, J., and Brady, T. J., Receptor-Directed Contrast Agents for MR Imaging: Preclinical Evaluation With Affinity Assays, Radiology, 182, 565–569 (1992), and Weissleder, R., Reimer, P., Lee, A. S., Wittenberg, J. and Brady, T. J., MR Receptor Imaging: Ultrasmall Iron Oxide Particles Targeted to Asialoglycoprotein Receptors, AJR, 155, 1161–67, (1990).

Antibody MR imaging has been described by Unger, E. C., Totty, W. G., Neufeld, D. M., Otsuka, F. L., Murphy, W. A., Welch, M. S., Connett, J. M., and Philpott, G. W., Magnetic Resonance Imaging Using Gadolinium labeled Monoclonal Antibody, Invest. Radiol., 20, 693–700. (1985), and Weissleder, R., Lee, A. S., Fischman, A. J., Reimer, P., Shen, T., Wilkinson, R., Callahan, R. J., and Brady, T. J., Polyclonal Human Immunoglobulin G Labeled with polymeric Iron Oxide: Antibody MR Imaging, Radiology, 181, 245–249, (1991). In the former case, one is limited by the amount of contrast enhancement that can be achieved by direct attachment of chelator to an antibody. In the latter case, the iron oxide particle is not amenable to control over surface functionality needed to reduce non specific adhesion and the particle is not well characterized or well tolerated in vivo.

SUMMARY OF THE INVENTION

This invention relates to nanoscale polymerized liposome particles based upon lipids having a polymerizable functional group and a metal chelator to attach an imaging enhancement agent, such as paramagnetic or radioactive ions, which assemble to form imaging enhancement polymerized liposomes. In preferred embodiments, the imaging enhancement polymerized liposomes are derivatized with antibodies and/or ligands for in vivo binding to cell surface receptors of targeted cells. In particular, these receptors can be located on the endothelium which eliminates the need for distribution of the active agent out of the blood pool. Paramagnetic polymerized liposomes according to this invention have been found to be well tolerated by rats, even on repeated administration, and effectively recirculate in the bloodstream, avoiding rapid endocytosis by the reticuloendothelial system. These materials provide good magnetic resonance imaging signal enhancement of targeted cells, liver and kidney, for long periods of time, of 90 minutes and more.

The polymerized liposomes of this invention are stable in vivo and provide for effective control of particle size, surface functionality, active ion density and water accessibility to maximize their effective relaxivity for T1 and T2* magnetic resonance imaging enhancement of specific biological systems. For example, the polymerized liposomes of this invention may have a plurality of metal ions for high relaxivity per particle providing highly effective magnetic resonance imaging enhancement and may also have attached antibodies or ligands specific for cellular receptors, resulting in a sensitive probe for areas of vascular tissue expressing these cell surface molecules. Receptors of protein adhesins on the endothelium surface are of particular interest in this targeting scheme because they are expressed extensively during pathological processes of inflammation for the recruitment of leukocytes or in the process of angiogenesis for vascularization of diseased tissue, such as tumors. Targeted polymerized liposomes provide for in vivo magnetic resonance imaging histology that enables early evaluation of changes in the endothelium in disease processes due to the attachment of a high concentration of paramagnetic or superparamagnetic ions to specific receptors on specifically targeted tissue or endothelium of concern.

BRIEF DESCRIPTION OF THE DRAWINGS

The file of this patent contains one drawing executed in color (FIG. 8). Copies of this patent with color drawing will be provided by the Patent and Trademark Office upon request and payment of the necessary fee.

The invention will be described in detail with reference to the drawings wherein.

DESCRIPTION OF PREFERRED EMBODIMENTS

The paramagnetic polymerized liposomes of this invention are self-assembled aggregates of lipid molecules which offer great versatility in particle size and surface chemistry. The size of the polymerized liposomes can be controlled by extrusion. The paramagnetic polymerized liposomes can be a mixture of lipids which provide different functional groups on the hydrophilic exposed surface. For example, some hydrophilic head groups can be a lanthanide-diethylenetriamine pentaacetic acid chelate for coupling a metal which provides for the paramagnetism and magnetic resonance contrast properties or for chelation of radioactive isotopes or other imaging materials. Other hydrophilic head groups can be, for example, biotin, amines, carboxylic acids, isothiocyanates, or hydrazine derivatives for coupling biological molecules, such as antibodies, peptides, or carbohydrate ligands providing for specific targeting and attachment to desired cell surface molecules. These lipids can be combined in varied proportions to produce paramagnetic or radioactive polymerized liposomes with a broad spectrum of chemical and biological properties. The magnetic resonance imaging R1 and R2* relaxivities can be controlled by the nature of the metal chelate and the distance of the metal from the surface of the particle. The hydrophobic tail groups of the lipids are derivatized with polymerizable groups, such as diacetylene groups, which irreversibly cross-link, or polymerize, when exposed to ultaviolet light or other radical, anionic or cationic, initiating species, while maintaining the distribution of functional groups at the surface of the liposome. The resulting polymerized liposome particle is stabilized against fusion with cell membranes or other liposomes and stabilized towards enzymatic degradation. In this manner, many thousands of active lanthanide ions or radioisotopes may be attached to one particle that may also bear several to hundreds of ligands for in vivo adherence to targeted surfaces. For T1 contrast agents the polymerized liposomes suitably have about 0 to about 30 percent metal chelating lipids, while for T2* contrast agents the polymerized liposomes have about 50 to about 99 percent metal chelating lipids. The large number of lanthanide ions renders the paramagnetic polymerized liposomes of this invention very sensitive magnetic resonance contrast agents with high R1 and R2* molar relaxivities while the multiple ligand binding sites improves in vivo binding affinity and specificity. This improved binding can also be utilized to block cell adhesion to endothelial receptors in vivo. Blocking these receptors can be useful to control pathological processes, such as inflamation and control of metastatic cancer. For example, multi-valent sialyl Lewis X derivatized liposomes can be used to block neutrophil binding and antibodies against VCAM-1 on polymerized liposomes can be used to block lymphocyte binding, for example T-cells.

Figure 1:
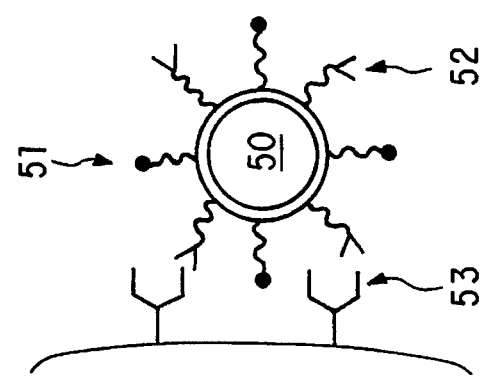
FIG. 1 schematically shows the action of targeted paramagnetic polymerized liposomes according to this invention.

FIG. 1 schematically shows the action of the polymerized liposome contrast agents of this invention. Polymerized liposome contrast agent core 50 has attached to its exterior surface contrast ions 51 for imaging enhancement, such as $Gd^{3+}$ for T1 MRI agents, $Dy^{3+}$ for T2* MRI agents and Tc or In ions for radioisotope imaging, and targeting groups 52, such as antibodies and ligands, tailored for attachment to cell surface molecules 53, such as receptors, ligands and antigenic determinants.

Suitable polymerized liposomes for use in this invention are those in which a contrast agent, paramagnetic ion or radioisotope, is provided at the surface of the particle. Preferably, the surface of the particle also carries a group to control nonspecific adhesion and reticuloendothelial system uptake with an agent to target the particle to areas of pathology, providing identification of changes in the endothelium during disease and to sequester the liposome in these areas without the need for the particle to leave the circulatory system. The polymerized liposomes of this invention provide: controlled surface functionality to prolong blood pool half life or cause the particle to leave the circulatory system, as desired; a targeting group, such as a ligand or antibody, to direct the particle to the desired region of interest; and a contrast enhancement material, such as a paramagnetic ion for MRI, a radioisotope, such as Tc or In, for radioisotope imaging, or a heavy metal, such as lead or barium, for standard x-ray analysis or a chromophore for optical imaging, to detect the presence of the particles in vivo.

The component lipids of the polymerized liposomes of this invention may be purified and characterized individually using standard, known techniques and then combined in controlled fashion to produce the final particle. The exposed surface of the polymerized liposomes of this invention can be constructed to mimic native cell membranes or present functionality, such as ethylene glycol derivatives, that can reduce their potential immunogenicity. Additionally, the polymerized liposomes of this invention have a well defined bilayer structure that can be characterized by known physical techniques such as transmission electron microscopy and atomic force microscopy.

Figure 3:
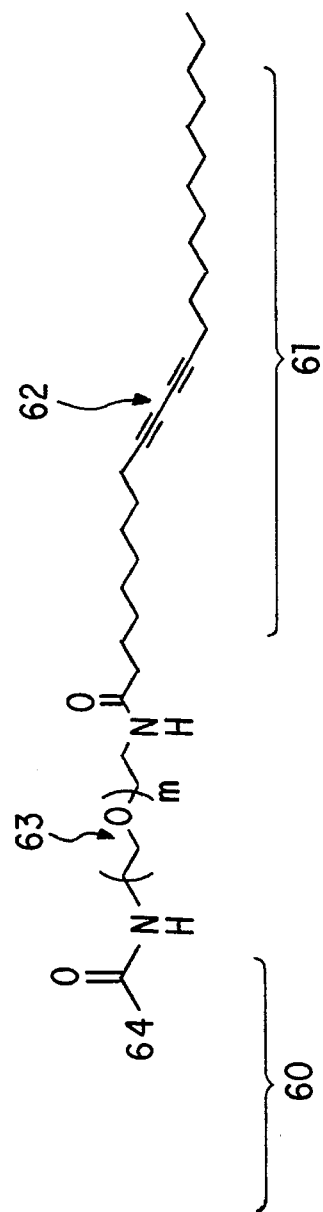
FIGS. 2 and 3 schematically show polymerizable lipid molecules according to one embodiment of this invention.
Figure 2:
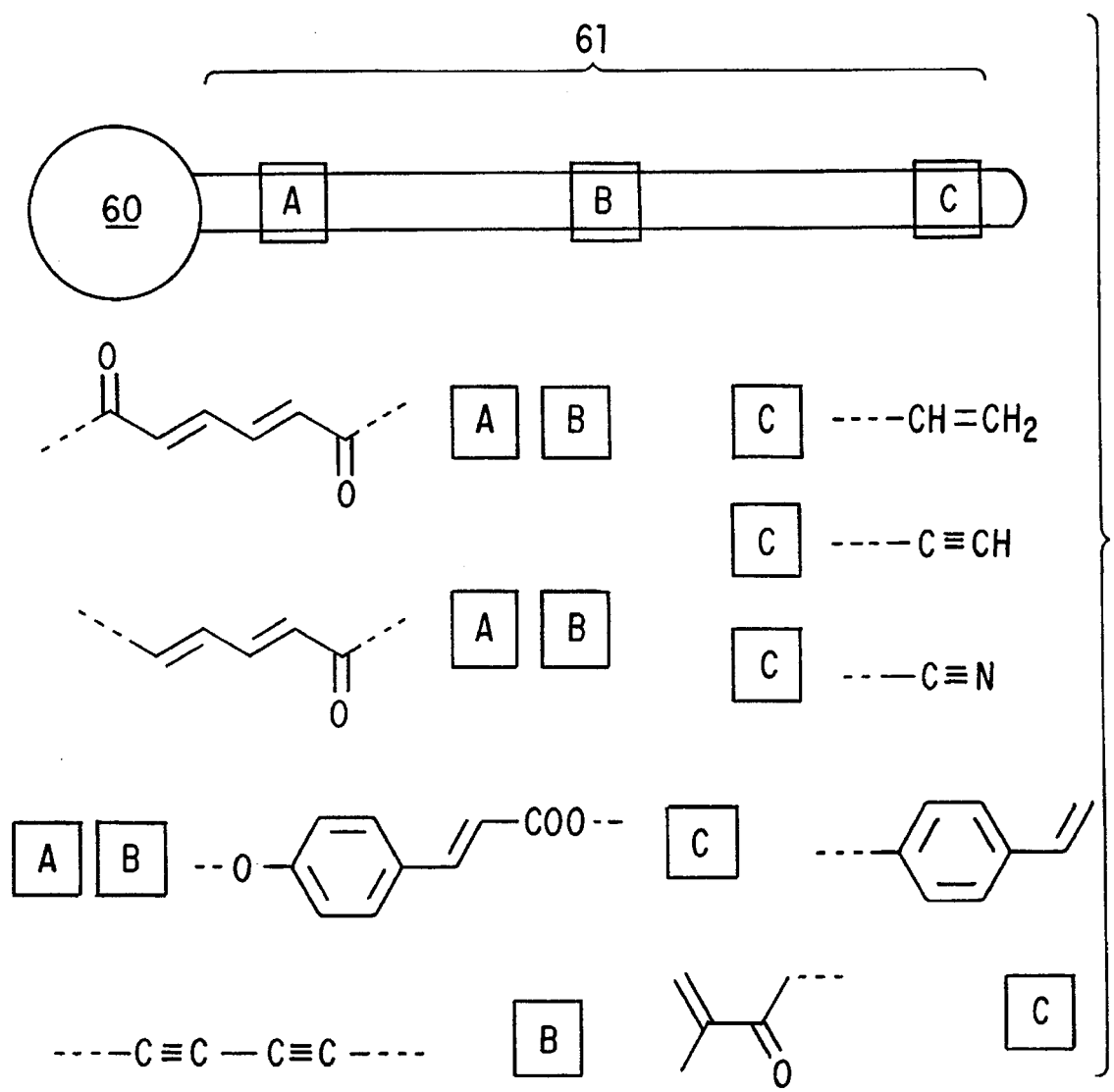

FIGS. 2 and 3 schematically show a polymerizable lipid molecule for use in this invention. The amphiphilic lipid molecule has a polar head group 60 and a hydrophobic tail group 61. The tail portion of the lipid has a polymerizable functional group 62, such as diacetylene, olefins, acetylenes, nitriles, styrenes, esters, thiols, amides and $\alpha$, $\beta$ unsaturated ketones, esters, amides and aldehydes forming liposomes which will polymerize upon irradiation with UV light or by chemical or thermal means. FIG. 2 shows polymerizable functional groups which may be located at specific positions A, B and C on tail group 61. As shown in FIG. 3, the head group and tail group are joined by variable length linker portion 63, such as variable length polyethylene glycol, polypropylene glycol, polyglycine, bifunctional hydrocarbon linker, for example amino caproic acid, or bifunctional aromatic compounds. The length of the linker portion, indicated by m, controls the distance of the active agent from the surface of the particle. The head group has a functional surface group 64, such as diethylenetriamine pentaacetic acid (DPTA), ethylenedinitrile tetraacetic acid (EDTA), tetraazocyclododecane 1,4,7,10-tetraacetic acid (DOTA), cyclohexane-1,2-diamino-N,N'-diacetate (CHTA) for chelating a paramagnetic or radioactive intensifying agent for contrast enhancement, or biotin, amines, carboxylic acids and hydrazine derivatives for coupling biologically active targeting agents, such as ligands, antibodies, peptides or carbohydrates for specific cell surface receptors or antigenic determinants.

Generally, the lipids suitable for use in this invention have: an active head group, for image contrast enhancement or for targeting, a linker portion for accessibility of the active head group; a hydrophobic tail for self-assembly into liposomes; and a polymerizable group to stabilize the liposomes.

Figure 4:
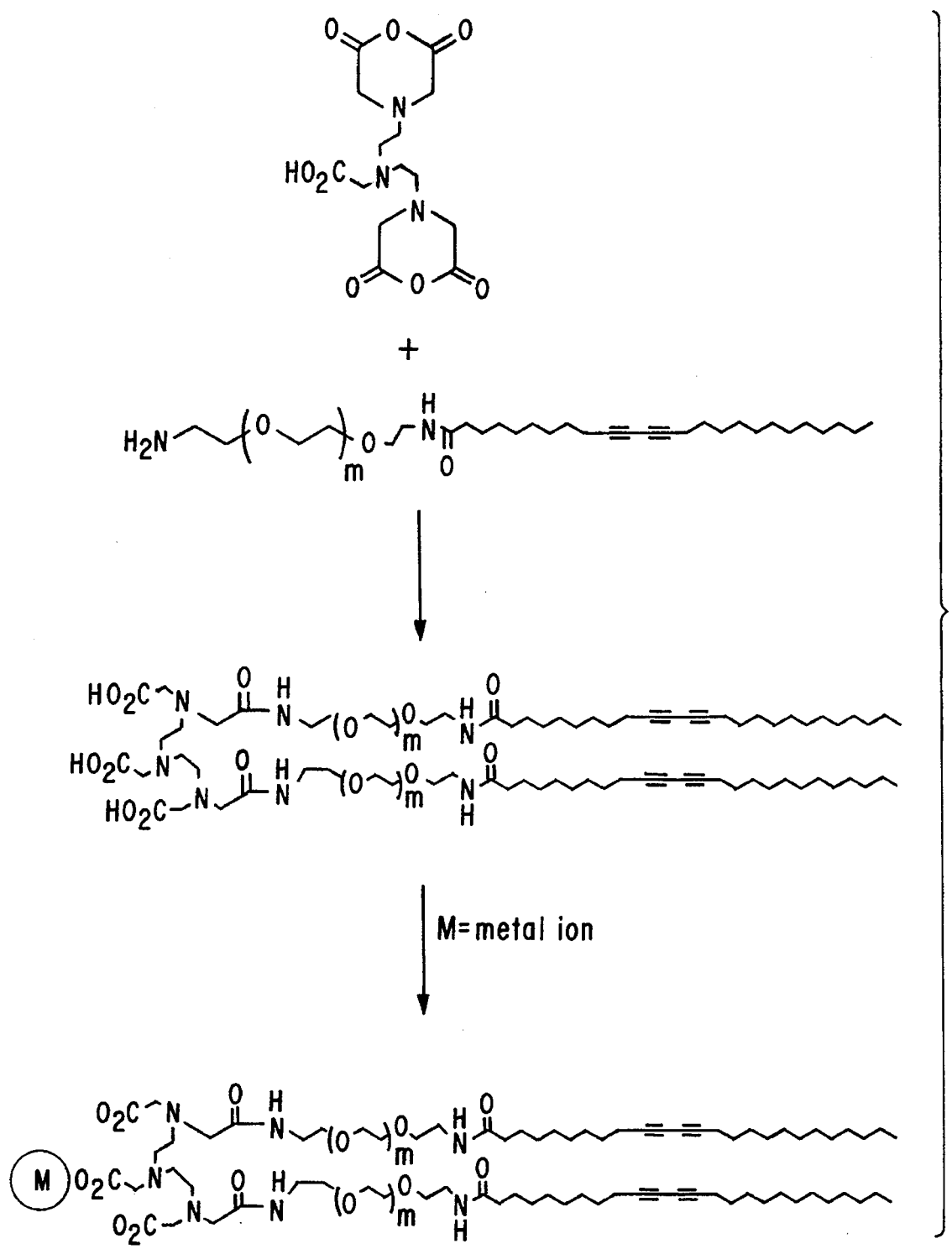
FIG. 4 shows the synthesis of a metal chelated lipid according to one embodiment of this invention.

A unique lipid is synthesized containing pentacosadiynoic acid conjugated to diethylenetriamine pentaacetic acid via a variable length polyethylene glycol linker as shown in FIG. 4. These amphipathic molecules have metal chelates as head groups connected to a lipid tail which contains a polymerizable diacetylene moiety. The linker length can be controlled by the choice of commercially available variable length polyethylene glycol derivatives.

Figure 5:
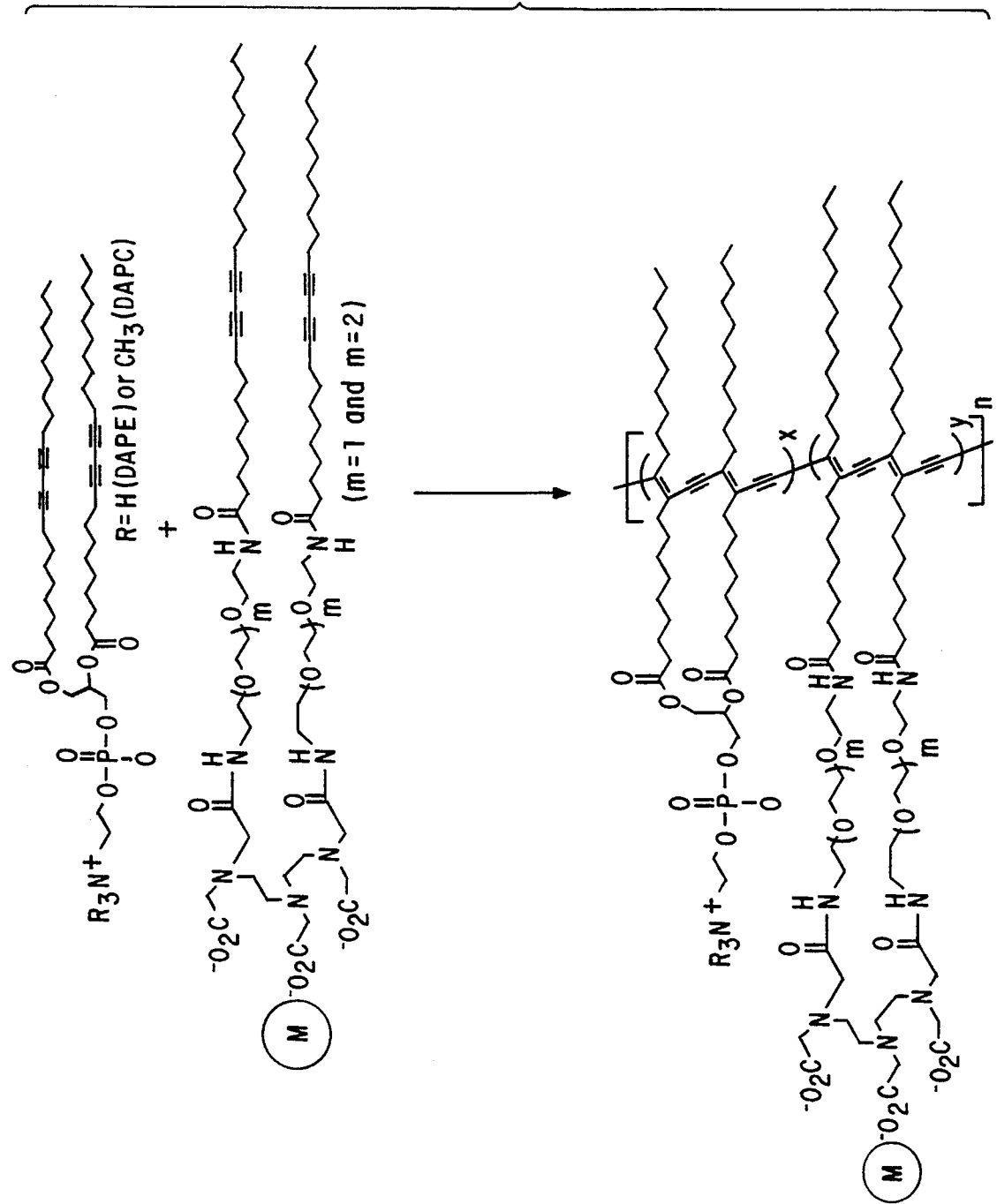
FIGS. 5 and 6 show formation of paramagnetic polymerized liposomes from the metal chelated lipid shown in FIG. 4 with filler lipids DAPC, DAPE or PDA according to one embodiment of this invention.

Specifically, we have synthesized compounds, such as shown in FIG. 4, by reacting the NHS ester of the lipid pentacosadiynoic acid (PDA) with triethyleneglycol-diamine and tetraethyleneglycol-diamine linkers to form the corresponding $PEG_m$-PDA amides, m=1 or 2, then reacting the $PEG_m$-PDA amide with diethylenetriamine pentaacetic acid dianhydride (DTPAA) to form diethylenetriamine pentaacetic acid-bis(tri or tetraethylene glycol-pentacosadiynoic acid) diamide (DTPA-bis-($PEG_m$-PDA), m=1 or 2 diamide). The diamide is then treated with a metal ion source M, such as gadolinium trichloride, dysprosium trichloride or a technicium or indium derivative to form the amphiphilic metal chelate as shown in FIG. 4 with a polyethylene linker (m=1 and m=2). The diamide-lanthanide chelate, shown in FIG. 4 and as a reactant in FIG. 5, is mixed with a matrix lipid of diacetylenic choline (DAPC, R=$CH_3$) or diacetylinic ethanolamine (R=H), shown in FIG. 5, pentacosadiynoic acid (PDA) or derivatives of PDA in an amount to result in the desired surface density of contrast agent on the polymerized liposomes. The matrix lipid forms polymerizable liposomes under a variety of conditions and closely mimics the topology of in vivo cell membranes.

Figure 6:
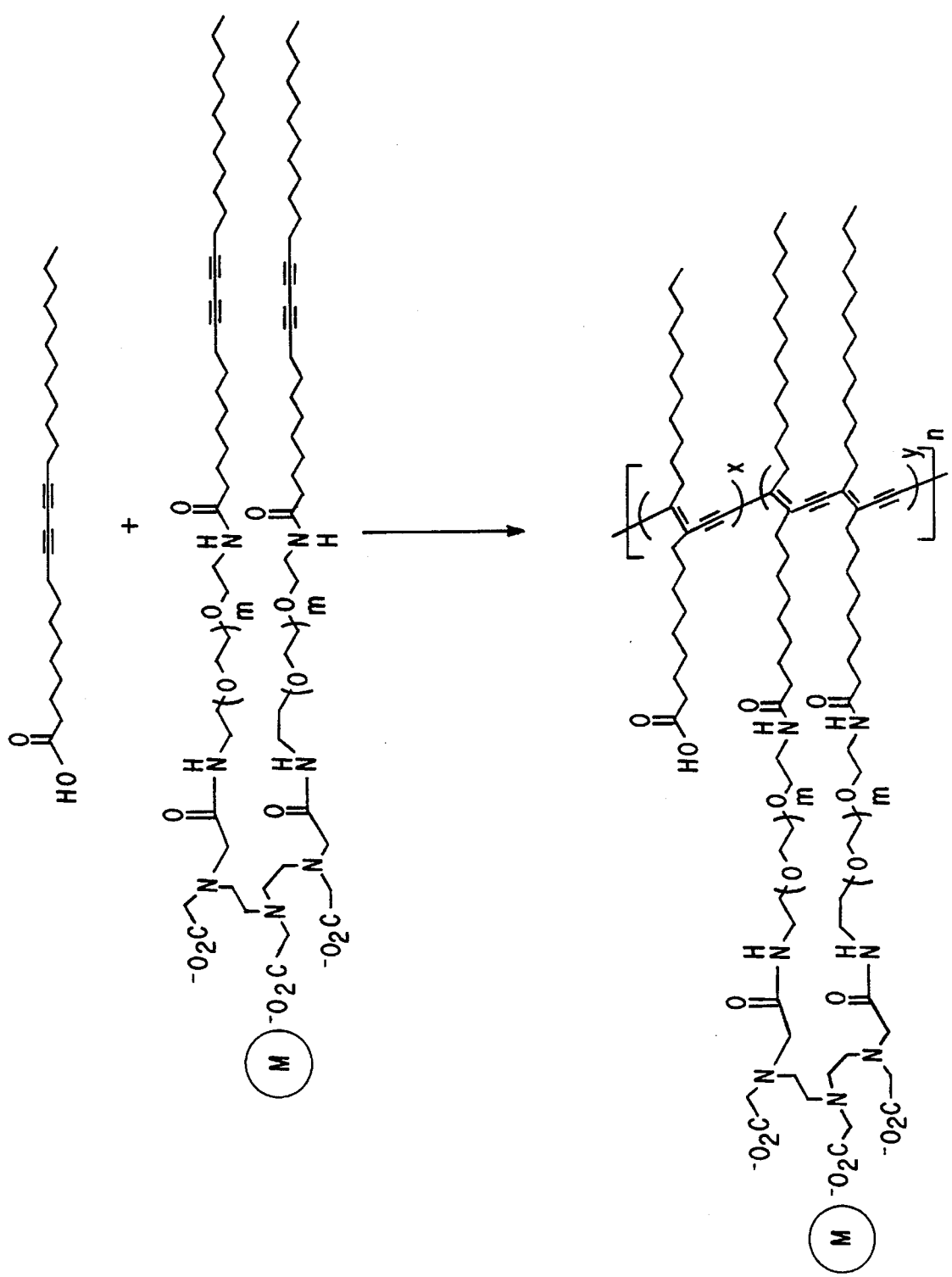

To form the paramagnetic polymerized liposome shown as the product in FIGS. 5 and 6, the metal chelated diamide shown in FIG. 4 is doped into the DAPC, as shown in FIG. 5, or PDA, as shown in FIG. 6, matrix in organic solvent. The organic solvent is evaporated and the dried lipid film is hydrated to a known lipid density, such as 15 mM total lipid, with the desired buffer or water. The resulting suspension is sonicated at temperatures above the gel-liquid crystal phase transition for DAPC or PDA, $T_m \approx 40°$ C. with a probe-tip sonicator. A nearly clear, colorless solution of emulsified vesicles, or liposomes, is produced. We have determined by transmission electron microscopy and atomic force microscopy that these liposomes are on average 30 to 200 nm in diameter. Their size can be reduced by extrusion at temperatures greater than $T_m$ through polycarbonate filters with well defined porosity. The liposomes are polymerized by cooling the solution to 4° C. on a bed of ice and irradiating at 254 nm with a UV lamp. Alternatively, the liposomes can be irradiated at room temperature and then cooled while continuing UV irradiation. The resulting paramagnetic polymerized liposomes, diagramatically shown as the products in FIGS. 5 and 6, are orange in color when using DAPC with two visible absorption bands centered at 490 nm and 510 nm arising from the conjugated ene-yne diacetylene polymer and generally blue in color when using PDA with absorption bands around 540 nm and 630 nm. These liposomes can undergo a blue to red transition when molecules bind to their surface after heating or resonication or after standing at room temperature for extended times or being treated with organic solvents. This transition may be useful for developing a detection system for these conditions.

We have constructed paramagnetic polymerized liposomes using the above techniques with 2.5 to 100 mol % of the gadolinium chelated diamide shown in FIG. 4, with the polyethylene glycol linker m=1 and m=2, and sizes ranging from 30 nm to 200 nm in diameter. We have determined the maximum T1 relaxivity, showing the best contrast, is obtained with 15% gadolinium chelated diamide and 85% DAPC with m=2 and having 200 nm particle size. High relaxivity is also observed with 30% gadolinium chelated diamide and 70% PDA with m=1 and having a variable particle size of about 10 to about 200 nm. Results of a variey of these measurements using DAPC matrix lipid are shown in Tables 1 and 2.

TABLE 1

| Gadolinium-diamide (%) | Size (nm) | R1 ($s^{-1}mM^{-1}$) | R2 ($s^{-1}mM^{-1}$) |
| --- | --- | --- | --- |
| 5.7 (m = 1) | 200 | 5.7 | Not Det. |
| 5.7 (m = 2) | 200 | 8.3 | Not Det. |
| 10 (m = 2) | 200 | 9.2 | Not Det. |
| 15 (m = 2) | 200 | 14.6 | Not Det. |
| 20 (m = 2) | 200 | 8.9 | Not Det. |
| 30 (m = 2) | 200 | 7.7 | Not Det. |
| 10 (m = 2) | 100 | 10.9 | 16.0 |
| 10 (m = 2) | 80 | 9.6 | Not Det. |
| 10 (m = 2) | 50 | 8.6 | 18.3 |
| 10 (m = 2) | 30 | 7.8 | 19.2 |
| Gd(DTPA)Magnevist, Berlix Lab., Wayne N.J. | | 4.4 | 1.9 |

To demonstrate the dependence on linker length, it is seen from Table 1 that when m=2 (R1=8.3) the metal ion appears to be suspended off the surface of the polymerized liposome allowing greater aqueous accessibility and hence greater relaxation than when m=1 (R1=5.7).

Similar measurements were made using PDA liposomes as the matrix lipid and the gadolinium chelated diamide (m=1). The results are shown in Table 2.

TABLE 2

| Gadolinium-diamide (%) | R1 ($s^{-1}mM^{-1}$) |
| --- | --- |
| 10 | 8.86 |
| 30 | 8.67 |
| 50 | 4.34 |
| 50* | 4.19 |
| 100 | 3.4 |

*1% biotin-DAPE

It is seen from Table 2 that liposome formulations of 10% and 30% metal chelator diamide and 90% and 70% PDA, respectively, exhibited the highest relaxivity of over 8 $mM^{-1}sec^{-1}$ while formulations of 50, and 100% metal chelator diamide had lower relaxivities. It is desired that the paramagnetic polymerized liposomes of this invention have a long half life in the recirculating blood pool to find their desired targeted receptors in vivo. To aid in retention in the blood pool, the overall size of the paramagnetic polymerized liposomes can be controlled and reduced by extrusion to reduce elimination from the blood pool by the reticuloendothelial system. Additionally, the surface chemistry of the polymerized liposomes can be modified to evade the hepatic and immune systems, for example, liposomes derivatized with polyethylene glycol decrease the rate of elimination by the reticuloendothelial system.

In a similar manner as described above with respect to FIGS. 5 and 6, dysprosium chelated lipids may be used to construct T2* untargeted or targeted paramagnetic polymerized liposomes according to this invention. Dysprosium is a desirable metal for T2* contrast since its magnetic susceptibility is the largest of any element and it is easily incorporated into a diethylenetriamine pentaacetic acid chelate. It may not be desired to use a matrix lipid to separate the paramagnetic metal centers, as found desirable for T1 paramagnetic polymerized liposomes. The chelator lipid described in FIG. 4 can be treated with dysprosium trichloride in sodium bicarbonate to produce the Dy-diacetylene lipid having M= $Dy^{+3}$ in FIG. 4. Single component paramagnetic polymerized liposomes can be constructed from these compounds by sonication, extrusion and polymerization in the manner described above, as shown in FIG. 6, with x=0. Alternatively, the dysprosium lipid reactant can be doped into DAPC, DAPE or PDA lipids at varying percentages.

For transmission electron microscopy (TEM), a polymerized liposome dispersion was deposited by freeze-drying onto the sample grid of the microscope and stained with osmium tetraoxide for 15 minutes. The micrograph shown as FIG. 7 was taken at a magnification of 21000 times and shows the polymerized liposome particles as ellipsoids having diameters of about 50 to 200 nm.

For Atomic Force Microscopy (AFM), samples were prepared by covering freshly cleaved mica with a solution of paramagnetic polymerized liposomes, 15 mM total lipid, for 1 to 2 minutes. The solution was recovered by pipet and the mica surface rinsed with a stream of distilled water. AFM images were obtained on an Explorer Life Sciences model 200 (Topometrix, Santa Clara, Calif.). The AFM was operated in the contact mode using the minimum force necessary to prevent hopping of the cantilever tip. The raw images were flattened either line-by-line or through a user-defined baseline plane, as appropriate, using software supplied by Topometrix. The paramagnetic polymerized liposomes, as shown in the AFM micrograph of FIG. 8, were readily observed as flattened ellipsoids with in-plane dimension similar to the 50 to 200 nm in diameter obtained by transmission electron microscopy (TEM). With non-extruded paramagnetic polymerized liposomes, smaller particles were more abundant than observed by TEM due to the higher resolution of AFM relative to TEM. The AFM provides more accurate sampling of particle sizes than TEM due to its higher resolution. Confidence in the uniformity of sampling particle sizes using AFM is enhanced since forward and reverse scanned images appeared identical within the reolution of the technique. We have found that AFM provides a simple and reliable method to assay particle sizes of the paramagnetic polymerized liposomes of this invention.

We have found that the metal chelate lipid, such as DTPA, is necessary to obtain images when mounting the sample on cleaved mica. Polymerized lipids lacking the metal chelate lipid did not produce AFM images using the above-described method. It is believed that the metal chelate lipid serves as a unique functionality for attachment of these materials to the mica, probably by chelating DTPA to metals on the cleaved mica. The metal chelate lipid molecule may be used to provide a unique functionality for attachment of other biomolecules to the surface of mica for AFM imaging.

Figure 9:
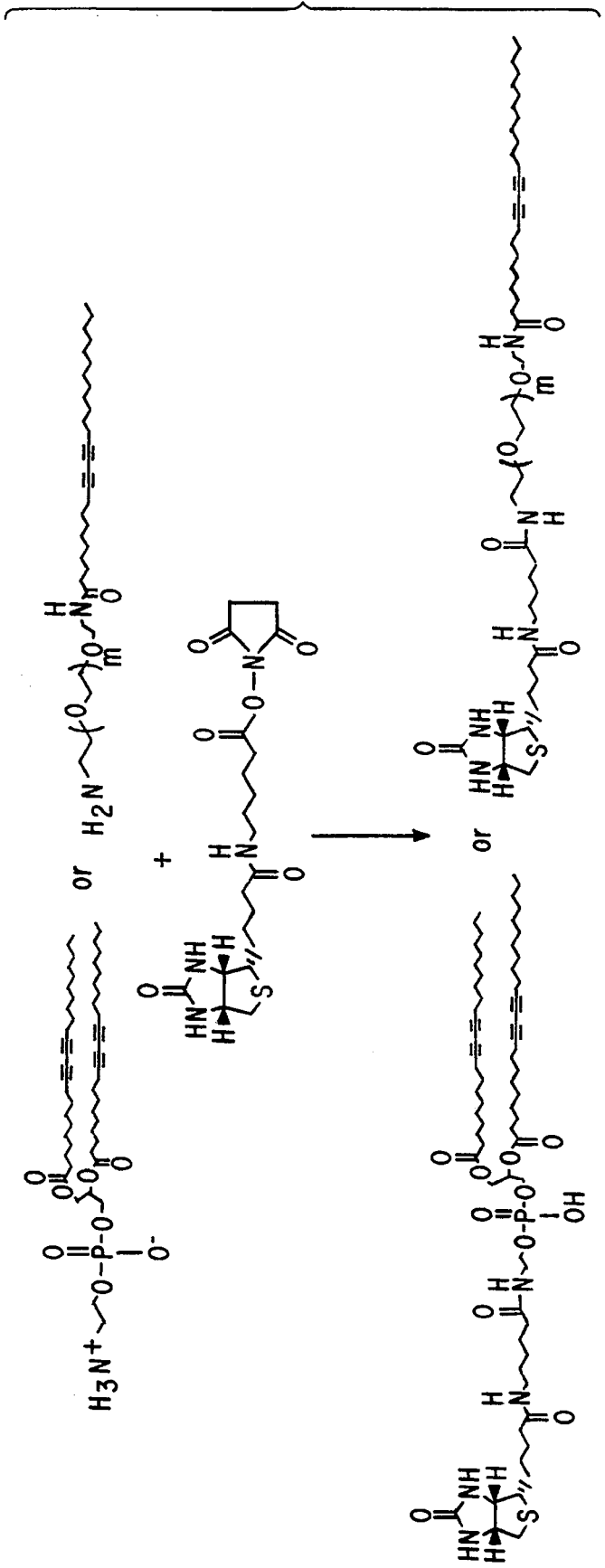
FIG. 9 shows the synthesis of biotinylated paramagnetic chelated lipids according to one embodiment of this invention.
Figure 10:
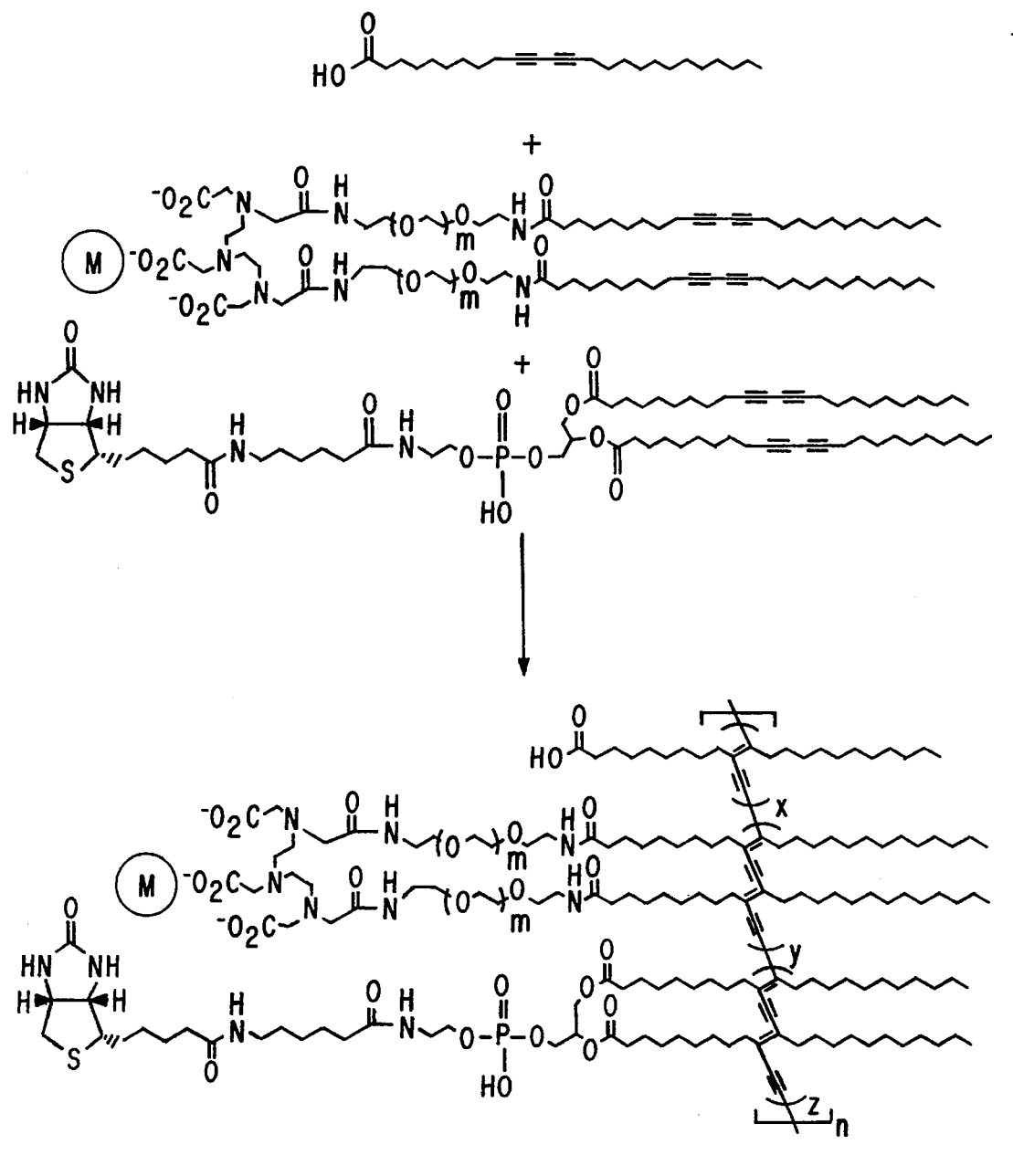
FIGS. 10 and 11 show formation of biotinylated paramagnetic polymerized liposomes using PDA and DAPC or DAPE.
Figure 11:
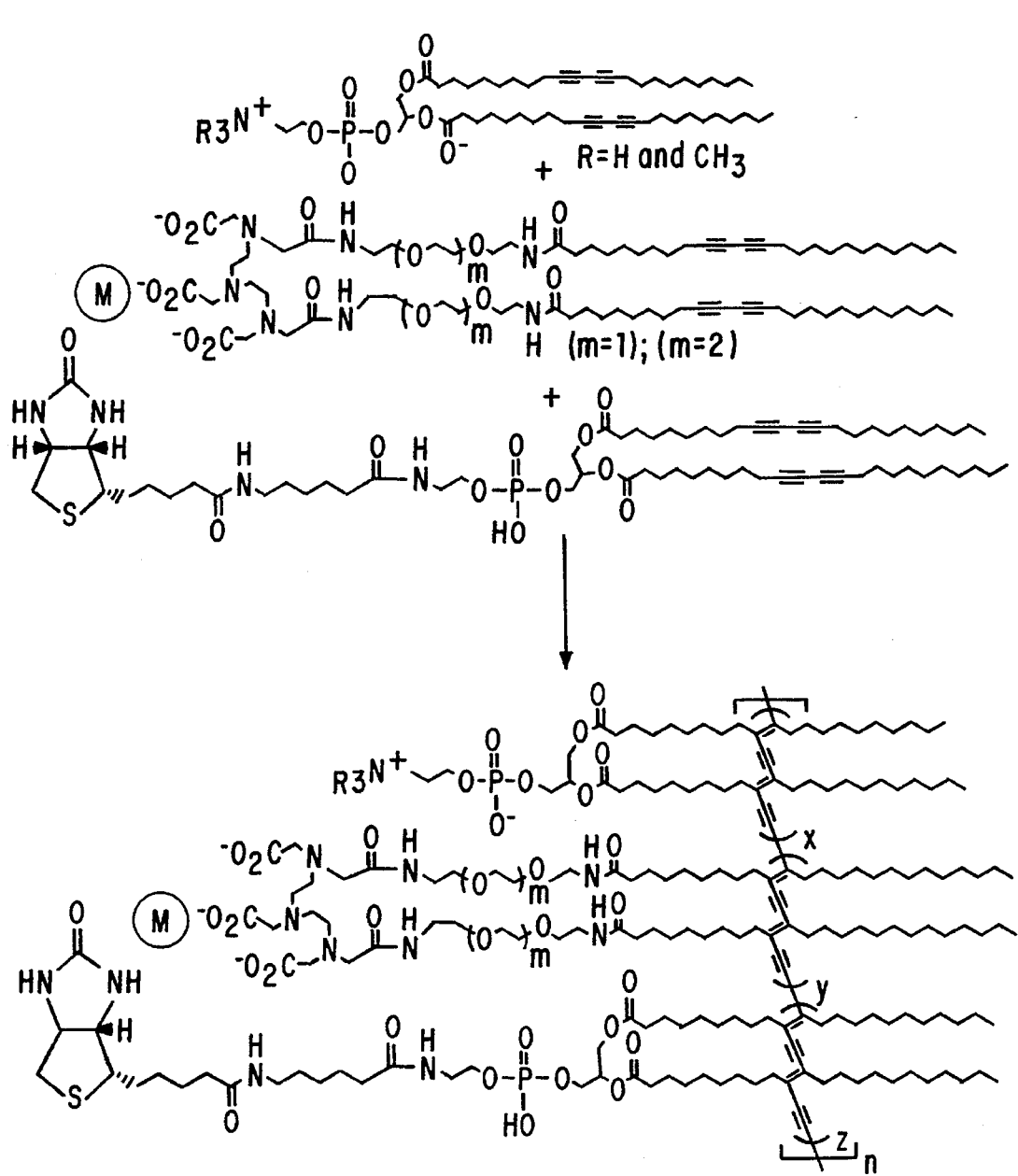

Targeted paramagnetic polymerized liposomes were produced from biotinylated liposomes to which biotinylated antibodies are attached through avidin, which has a high affinity for biotin, and the biotinylated antibody-avidin conjugate attached to the polymerized liposome. Commercially available diacetylene glycerophosphoethanolamine (DAPE) lipid is converted to its biotinylated analog by acylation of the amine terminated lipid with commercially available biotinylating agents, such as biotinamidocaproate N-hydroxysuccinimide ester or paranitrophenol esters, as shown in FIG. 9. The biotinylated paramagnetic polymerized liposomes are produced by incorporating the biotinylated lipid in an matrix of lipids of either PDA, DAPE or DAPC as shown in FIGS. 10 and 11, respectively.

Figure 12:
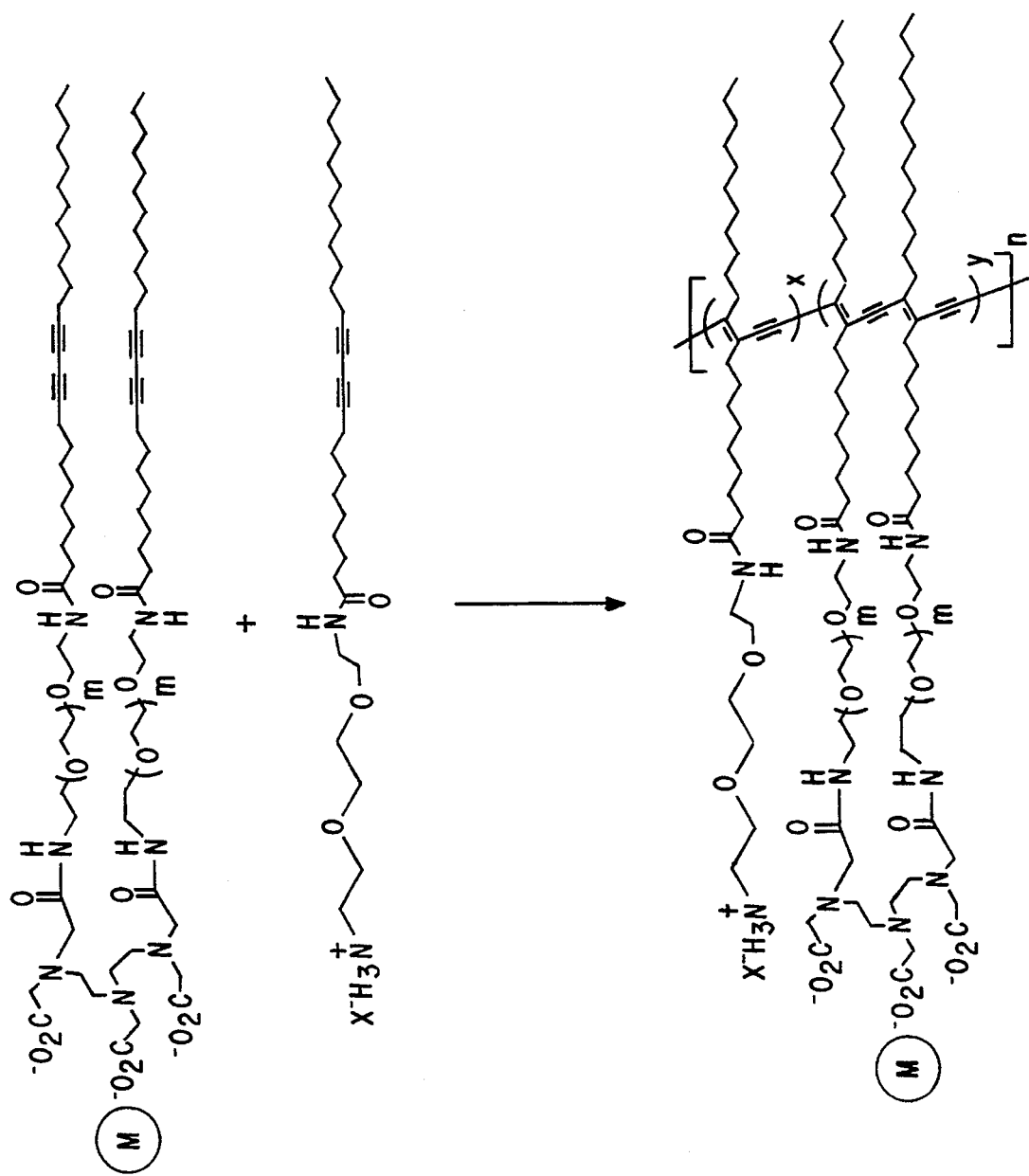
FIG. 12 shows formation of paramagnetic polymerized liposomes having positively charged functional groups.
Figure 13:
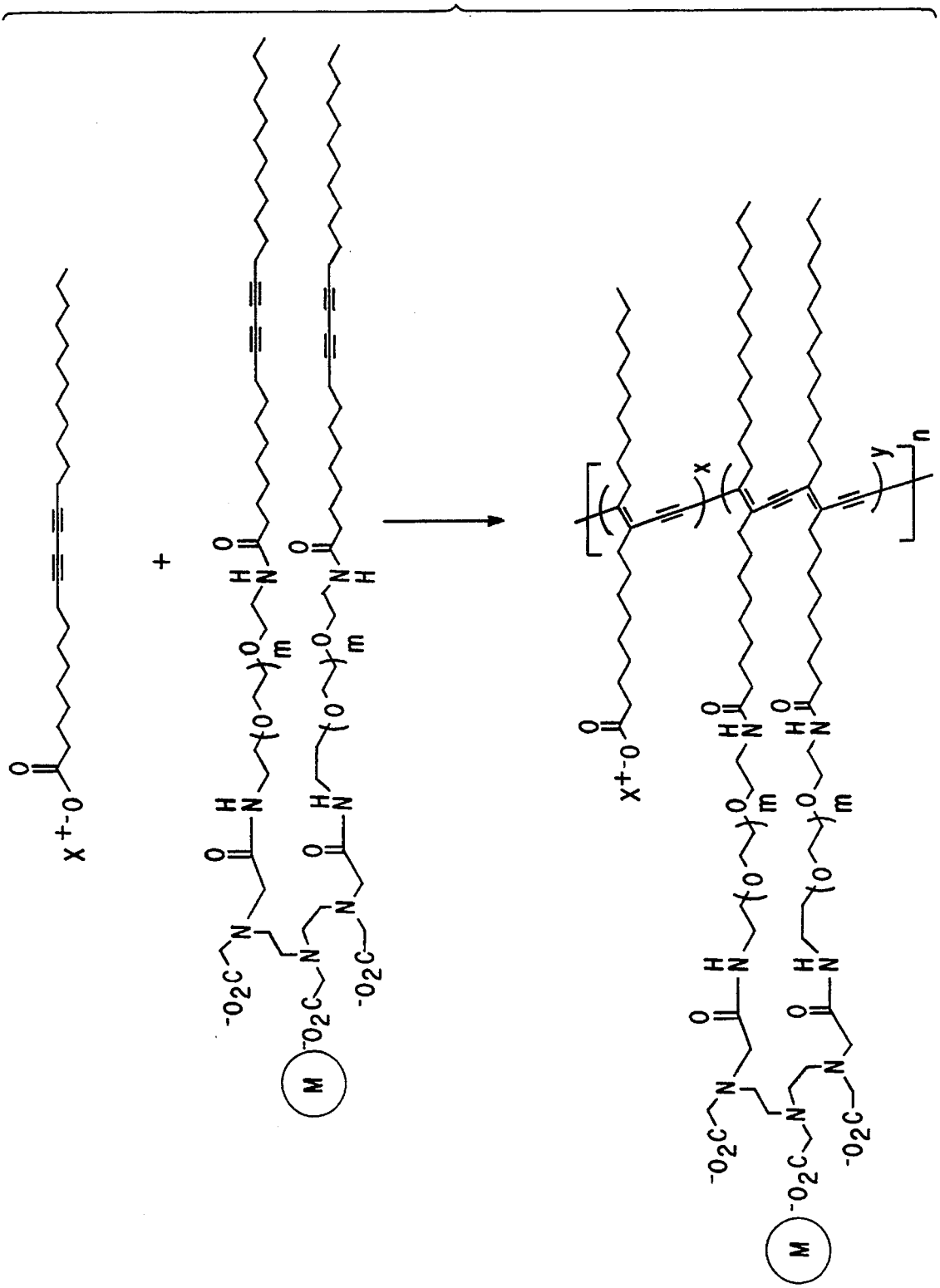
FIG. 13 shows formation of paramagnetic polymerized liposomes having negatively charged functional groups.
Figure 14:
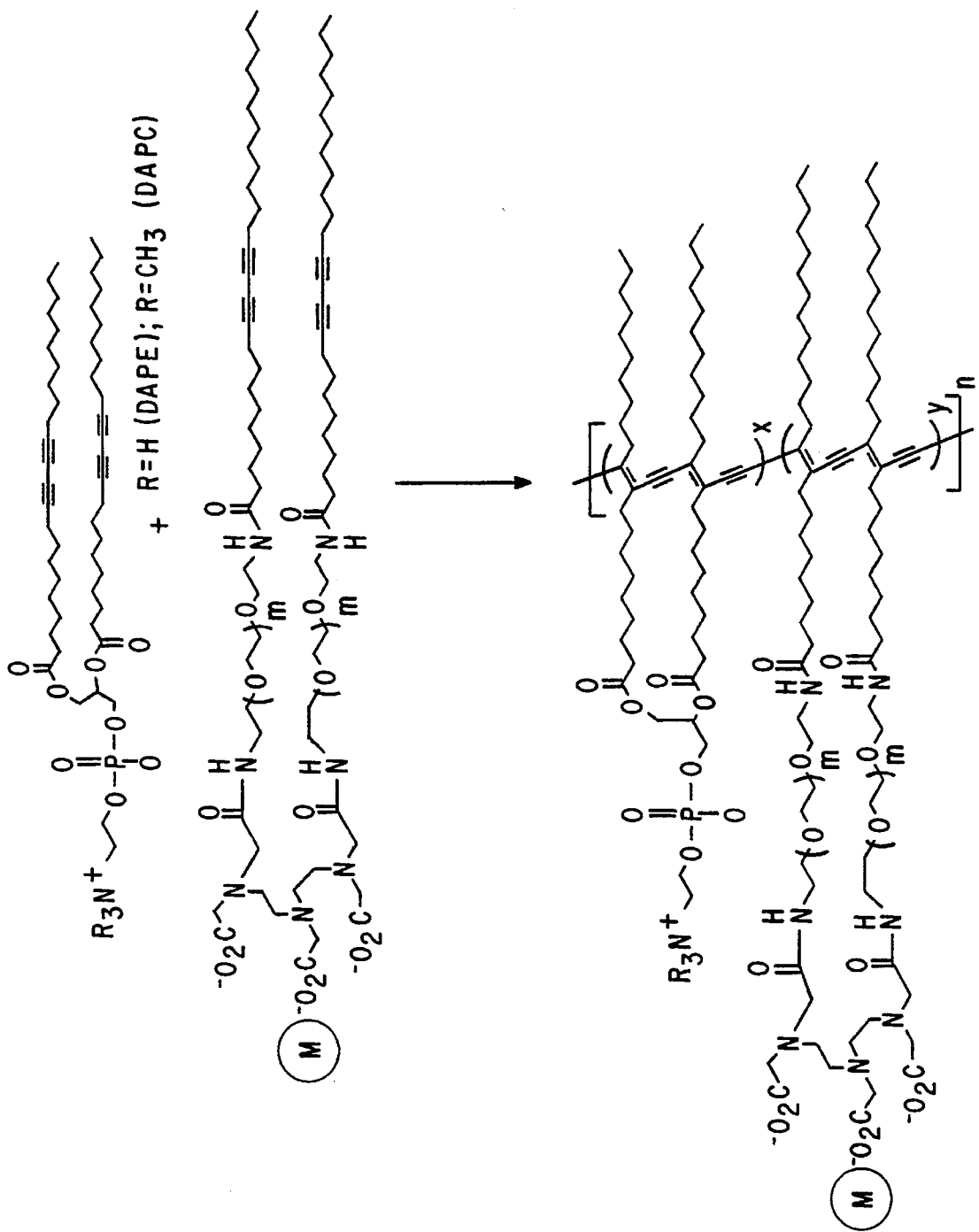
FIG. 14 shows formation of paramagnetic polymerized liposomes having zwitter ionic functional groups.

This invention includes a broad based group of agents having varied functionality which includes liposomes containing positively charged groups, such as amines as shown in FIG. 12, negatively charged groups, such as carboxylates as shown in FIG. 13, and neutral groups, such as zwitterions as shown in FIG. 14. These groups can be used to control biodistribution blood pool half-life and non-specific adhesion of the particles.

Figure 15:
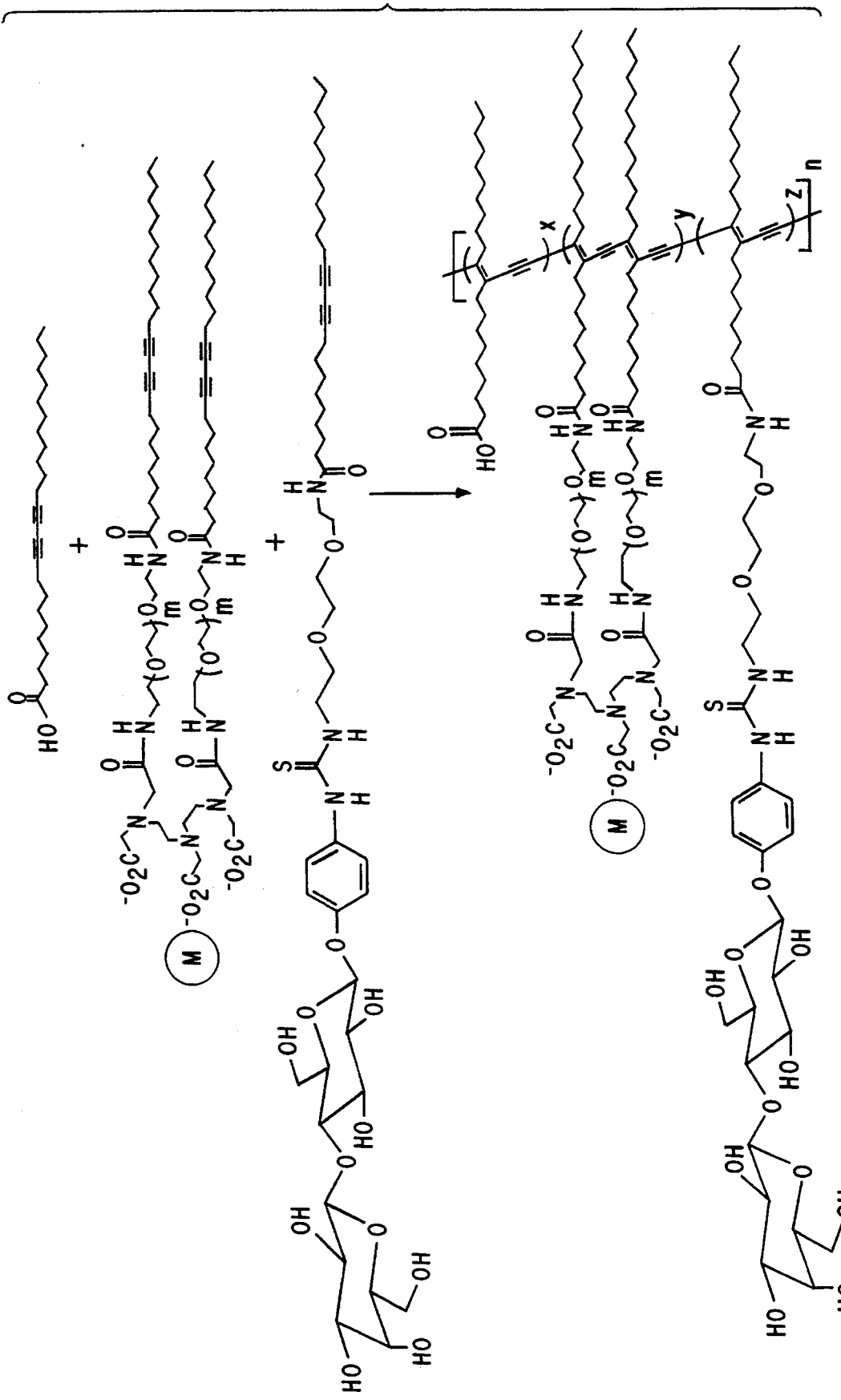
FIG. 15 shows formation of paramagnetic polymerized liposomes having lactose targeting groups.

Targeting groups of polymerized liposomes according to this invention may be ligands, such as carbohydrates, proteins, such as antibodies, peptides, antigenic determinants, or other receptor targeting groups. These head groups can be used to control the biodistribution, non-specific adhesion, and blood pool half life of the polymerized liposomes. For example, β-D-lactose has been attached on the surface, as shown in FIG. 15, to target the asaloglysoprotein (ASG) found in liver cells which are in contact with the circulating blood pool. Targeting glycolipids are formed by converting the commercially available lipid (DAGPE) or the PEG-PDA amine shown in FIG. 4 into its isocyanate followed by treatment with triethylene glycol diamine spacer to produce the amine terminated thiocarbamate lipid which by treatment with the para-isothiocyanophenyl glycoside of the carbohydrate ligand produces the desired targeting glycolipids. This synthesis provides a water soluble flexible linker molecule spaced between the lipid that will form the internal structure or core of the liposome and the ligand that binds to cell surface receptors, allowing the ligand to be readily accessible to the protein receptors on the cell surfaces. The carbohydrate ligands can be derived from reducing sugars or glycosides, such as para-nitrophenyl glycosides, a wide range of which are commercially available or easily constructed using chemical or enzymatic methods. Paramagnetic polymerized liposomes coated with carbohydrate ligands can be produced by mixing appropriate amounts of individual lipids followed by sonication, extrusion and polymerization and filtration as described above and shown in FIG. 15. Suitable carbohydrate derivatized paramagnetic polymerized liposomes have about 1 to about 30 mole percent of the targeting glycolipid and filler lipid, such as PDA, DAPC or DAPC, with the balance being metal chelated lipid. Other lipids may be included in the polymerized liposomes to assure liposome formation and provide high contrast and recirculation.

Figure 16:
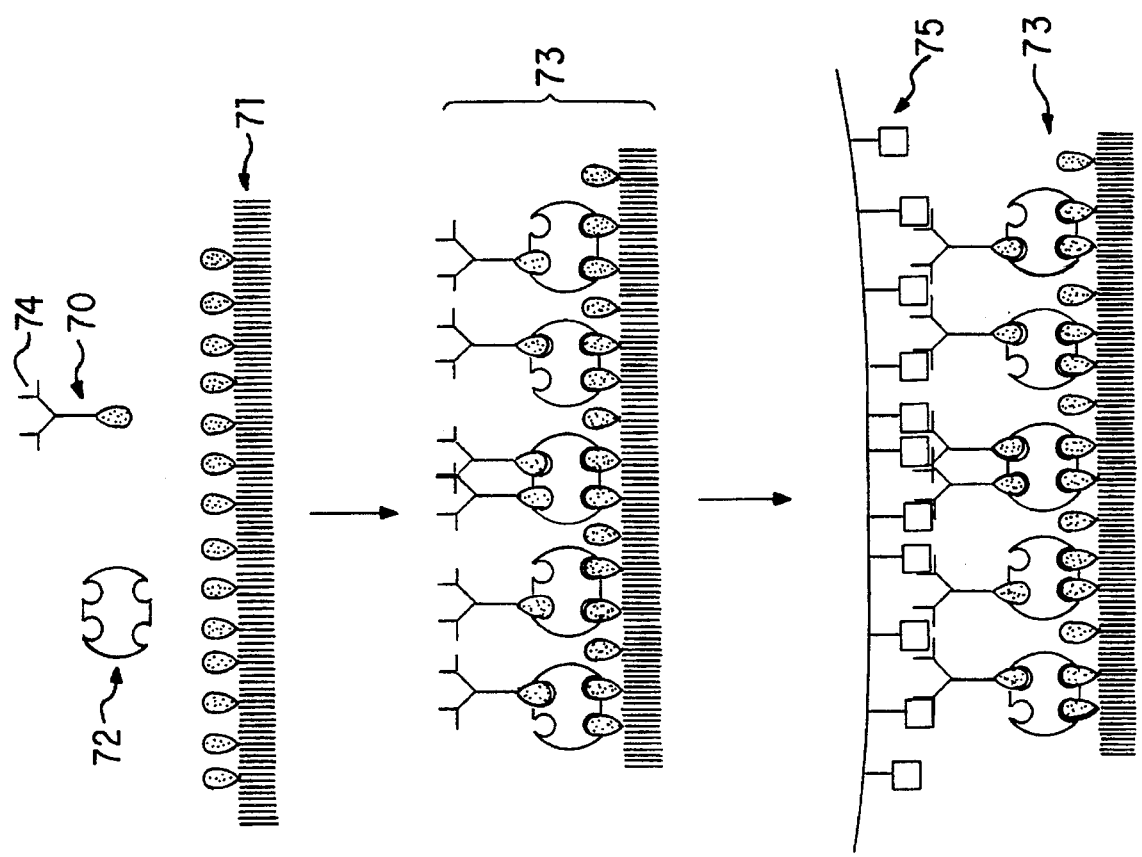
FIG. 16 schematically shows formation of paramagnetic polymerized liposomes having antibodies attached.

Antibodies may be attached to the particle by the biotin-avidin biotinylated antibody sandwich, as shown in FIG. 16, to allow a variety of commercially available biotintylated antibodies to be used on the polymerized liposome particles of this invention.

Biotinylated paramagnetic polymerized liposomes with a biotinylated anti-VCAM-1 antibody attached via a biotin avidin sandwich were produced in the manner described above. This targeted paramagnetic polymerized liposome binds to VCAM-1, a leukocyte adhesion receptor on the endothelial surface which is upregulated during inflammation. In vitro histology demonstrated specific interactions between the polymerized liposomes and the inflammed brainstem tissue from a mouse with allergic autoimmune encephalitis. The formation of such biotynilated antibody coated polymerized liposomes and their attachment to in vivo cell receptors is schematically shown in FIG. 16. As shown in FIG. 16, the biotinylated antibody 70 having functional group 74 is attached to the biotinylated lipid surface 71 through bridge 72 of avidin or streptavidin to form antibody coated polymerized liposomes 73. The functional group 74 of antibody 70 is attached in vivo to an endothelium receptor 75, thereby attaching the paramagnetic polymerized liposome to the endothelium for external detection.

Figure 17:
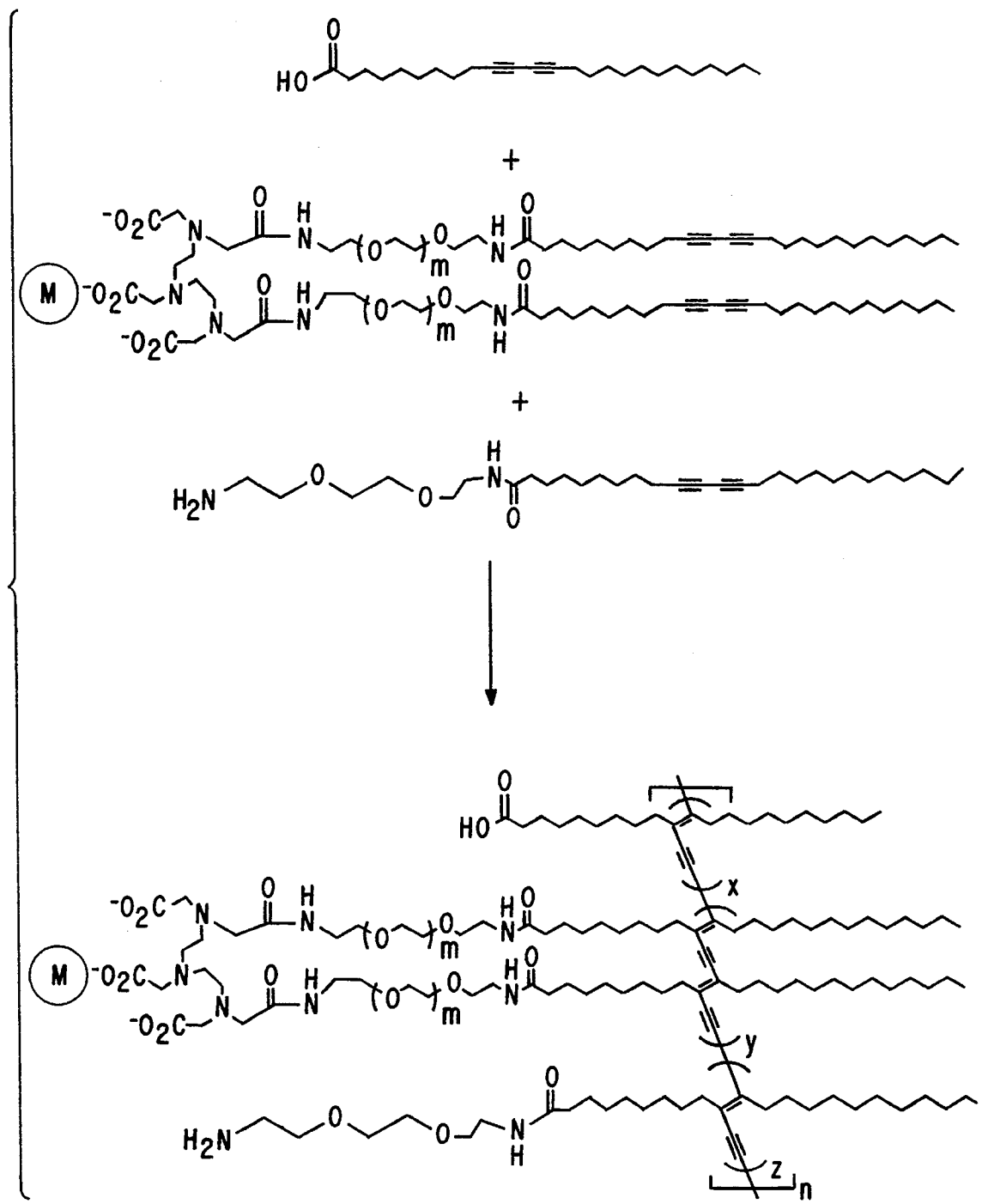
FIGS. 17 and 18 show formation of liposomes that can be used for direct attachment of oxidized antibodies by an amine via reductive amination and hydrazone formation via hydrazine derivatives.
Figure 18:
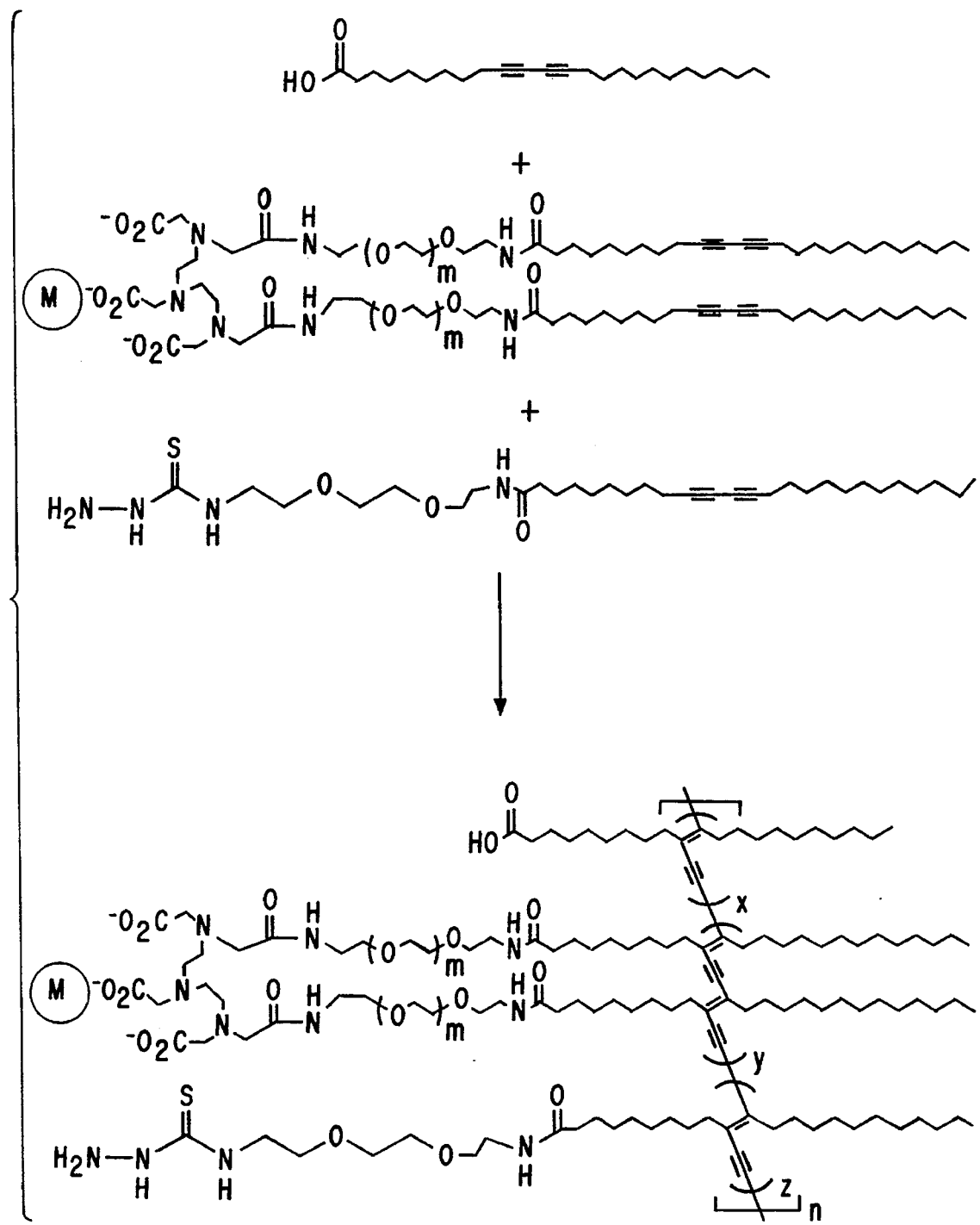

Antibodies may also be attached by "direct" methods. In particular, wherein the liposome contains a group, such as an amine or hydrazine derivatives, that reacts with aldehydes on oxidized antibodies and olgosaccharides. We have constructed liposomes containing amine, FIG. 17, and hydrazine, FIG. 18, head groups for this purpose.

Although this invention has been described and specifically exemplified primarily with respect to polymerized liposomes having an attached metal for magnetic resonance imaging, it should be clear to one skilled in the art that other detection materials may be attached in a similar manner, such as a radioisotope for radioisotope imaging, a heavy metal for x-ray imaging, or a chromophore for optical imaging and are meant to be included in this invention. Likewise, any suitable functional group may be attached to liposomes incorporated into the polymerized liposomes of this invention to provide attachment to specified targets, particularly in vivo, to obtain concentration of the image contrast agent at the specified target site.

The following specific examples are set forth in detail to illustrate the invention and should not be considered to limit the invention in any way.

EXAMPLE I

Paramagnetic polymerizable lipids having $Gd^{+3}$ and PDA headgroups were synthesized by first preparing the succinimidyl ester by stirring pentacosadiynoic acid (PDA, Lancaster; 10.0 g, 26.7 mmol), N-hydroxysuccinimide (NHS, Aldrich; 5.00 g, 43.4 mmol) and 1-(3-dimethylaminopropyl)-3-ethylcarbodiimide hydrochloride (EDC, Aldrich; 6.01 g, 31.3 mmol) in 660 ml $CH_2Cl_2$ at room temperature and shielded from light. The reaction was followed by thin layer chromatography ($CHCl_3$/MeOH, 8/1) and deemed complete after approximately 5 hours. The solution was washed with water, 1% HCl, saturated sodium bicarbonate and brine. The organic phase was then dried with $MgSO_4$, filtered, and concentrated under reduced pressure to yield the N-succinimidyl 10,12-pentacosadiynoic acid ester as a slightly yellow solid (10.84 g; 23.0 mmol; 86%).

The succinimidyl ester was dissolved in $CH_2Cl_2$ (250 ml) and then slowly added, in dropwise fashion, to a stirred solution of 1,11-diamino-3,6,9-trioxyundecane (9.13 g, 61.6 mmol; Texaco) in $CH_2Cl_2$ (110 ml) over a 16 hour period at room temperature and shielded from light. The resulting solution was concentrated to a thick slurry and chromatographed on silica gel using a gradient of $CHCl_3/MeOH$ (1/0 to 8/1). The homogeneous fractions were pooled and evaporated under reduced pressure to result in the desired lipid, (1'-N-,11'-amino-3',6'-dioxyundecanoyl)- 10,12-pentcosadiynamide, as a white solid (4.40 g; 38.1%). This product must be handled with care as it spontaneously polymerizes in the solid state when it is pure. It is more stable in solution at 4° C., but should be used as soon as possible after preparation.

The above-prepared aminoamide (4.40 g; 8.78 mmol) and DTPAA (1.56 g; 4.37 mmol) were stirred in pyridine (25 ml) overnight, shielded from the light. The solvent was evaporated and the residue coevaporated with methanol to dryness twice to result in an oil free from pyridine. The residue was dissolved in acetone and the product allowed to precipitate from solution after overnight storage at 4° C. Filtration resulted in the desired chelator lipid, bis-N-[ 2-ethyl-N-'carboxymethyl,N'-carboxymethyl( 1'-N-''',11'-N''''- 3', 6'-dioxyundecanoyl)amide-1'',12''-pentacosadiynamide]glycine, as a white amorphous powder containing minor impurities (3.30 g; 55%) Pure lipid (1.55 g; 26%) can be crystallized from methanol (40 mg/ml; m.p. 128.5°–129.5° C. (decomp.)).

The chelator lipid, as prepared above, was heated with $GdCl_3 \cdot 6H_2O$ or $DyCl_3 \cdot 6H_2O$ (0.95–0.98 equiv.) in methanol. The solvent was evaporated and the residue coevaporated with methanol to remove all traces of generated HCl. The resulting lanthanide chelate lipids, bis-N-[2-ethyl-N-'carboxymethyl,N'-carboxymethyl( 1'-N-''',11'-N''''- 3',6'-dioxyundecanoyl)amide- 1'',12''-pentacosadiynamide]-glycinelanthanide,gadolinium or dysprosium, complexes, were then stored as methanolic solutions at 4° C. shielded from light The identity of the synthesized chelates was confirmed by FAB-MS.

Paramagnetic polymerized lipids were formed by mixing a 1:9 molar ratio of the above prepared paramagnetic polymerizible lipids with di-tricosadiynoyl phosphatidyl choline (Avanti Polar Lipids, Birmingham, AL) in an organic solvent methyl alcohol and chloroform (⅓) and evaporating the solvent and rehydrating with distilled water to 30 mM diacetylene (15 mM total lipid). Following sonication with a 450 W probe-tip sonicator (Virsonic 475, Virtis Corp., Gardiner, N.Y.) set at a power setting of 2½ units for 30 to 60 minutes without temperature control, the suspension of lipid aggregates was extruded ten times through two polycarbonate filters with pores of 0.1 μm diameter (Poretics, Livermore, Calif.) at 56° C. using a thermobarrel extruder (Lipex Biomembranes, Vancover, BC). This solution was spread thinly on a petri dish in a wet ice slush and irradiated with a UV lamp , 2200 μWatt/cm² held 1 cm over the solution while stirring. The solution turned orange using DAPC over the course of a one hour irradiation, due to the absorption of visible light by the conjugated ene-yne system of the polymer. The paramagnetic polymerized liposomes passed easily through a 0.2 μm sterilizing filter and were stored in solution until use. The paramagnetic polymerized lipid suspensions prepared in this manner have been found to be stable for many weeks at 4° C.

Figure 7:
FIG. 7 is a transmission electron micrograph of polymerized liposome particles.
Figure 8:
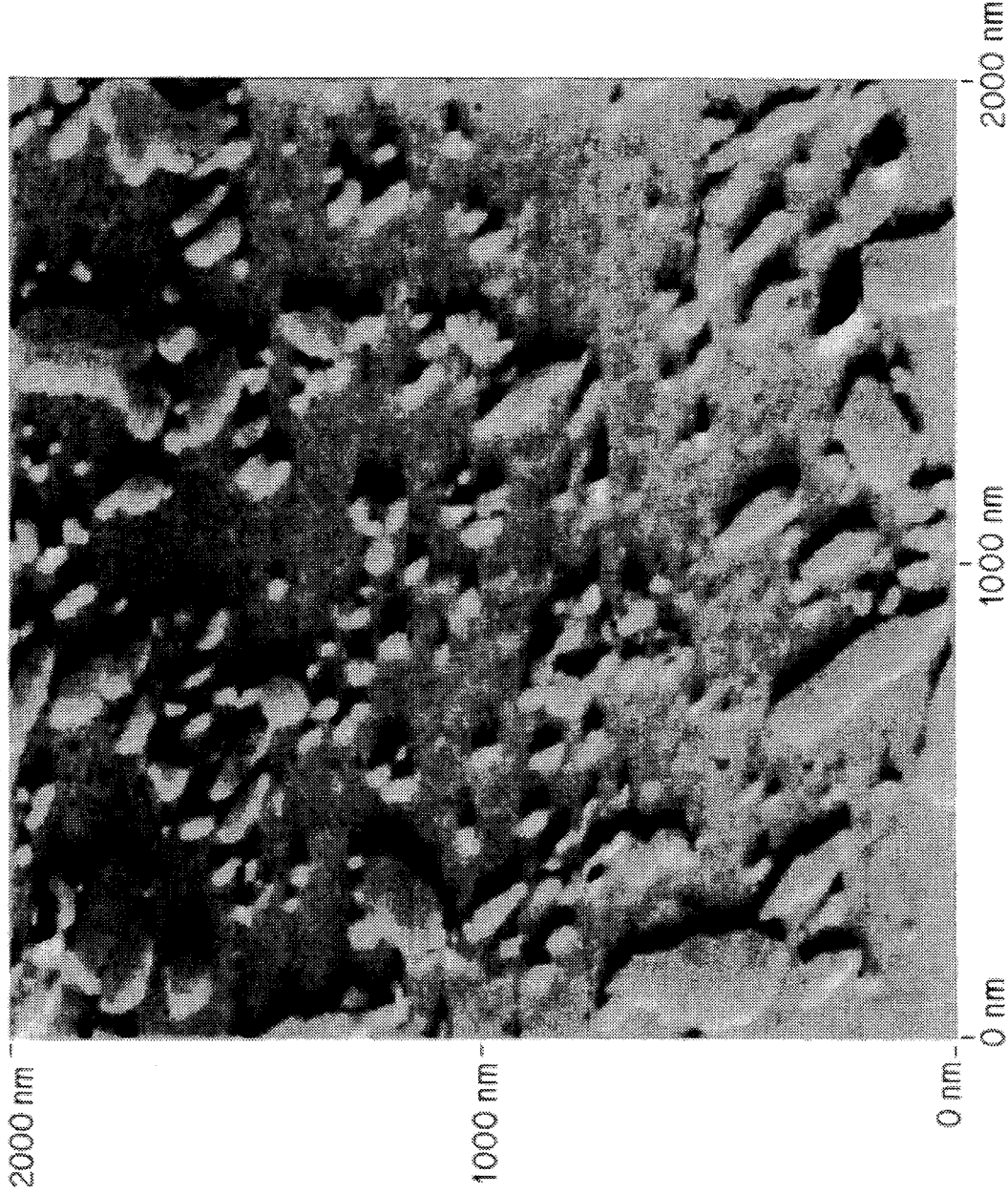
FIG. 8 is an atomic force micrograph of polymerized liposome particles.

The size and shape of the paramagnetic polymerized liposomes have been ascertained by transmission electron microscopy and by atomic force microscopy, as shown in FIGS. 7 and 8. They appear as prolate ellipsoids with minor axes on the order of the membrane pore and major axes about 50 percent greater.

EXAMPLE II

The procedures of Example I were followed except that instead of using DAPC, pentacosydiynoic acid (PDA) was used as the filler lipid. The solution turned blue over the course of one hour irradiation. The resulting polymerized liposomes had the same general properties as reported in Example I.

EXAMPLE III

Two month old Lewis rats were anaesthetized either with 40–75 mg/Kg dose of sodium pentobarbitol i.p. or by 1.5% isoflurane by inhalation. Paramagnetic polymerized liposome, as prepared in Example I, was administered i.v. over 60–90 seconds through a 24G catheter in a lateral tail vein at a dose of 0.015 mmol $Gd^{+3}$/kg body weight.

Axial magnetic resonance images of the abdomen were obtained prior to paramagnetic polymerized liposome administration and periodically for up to 2 hours post administration. All magnetic resonance images were obtained using an OMEGA-CSI imager (GE, Milwaukee, Wis.) at field strengths of 2.0 or 4.7 Telsa using the standard spin-echo acquisition sequence. T1 weighted images were obtained using a repetition time (TR) of 400 ms, echo time (TE) of 18 ms, and 2 excitations (NEX) per 128 phase encoding steps, completing a 256×128 data matrix in under 2 minutes. Slice thickness (ST) was 2 mm and the interslice gap was 2 mm. Four axial slices were acquired in multislice mode, with the slice position chosen so that the liver appeared in the first two slices and the kidneys appeared in the fourth, most inferior slice. These images were often supplemented by a second set of images interleaving the first set. Two phantoms, test tubes containing 10 mM $Ni(NO_3)$ or 1 mM $GdCl_3$, were placed longitudinally beneath the rats and were imaged concurrently to monitor instrumental variations. The image intensity of the phantoms varied less than 5% in all of the experiments.

Data analysis was performed using the program XCINEMA (Lucas MRS Center, Stanford University, Stanford, Calif.) Region of interests (ROI) were drawn conservatively within each organ, and the intensity of the same region at each time point was measured. The intensity data post contrast was normalized to the intensity of the ROI prior to contrast administration and the normalized data for each time point averaged across six experiments on four rats each.

The injected paramagnetic polymerized liposomes were well tolerated by the rats with no significant adverse effects observed. The rats continued to gain weight in the days succeeding administration and exhibited normal behavior and activity. Hematuria was observed only in the first urination following recovery from the anesthesia, likely as a result of osmotic shock since the injection preparation contained no added salts. Repeated administration of the paramagnetic polymerized liposome preparation to the same rat did not affect tolerance or contrast enhancement.

Figure 19:
FIGS. 19–21 are magnetic resonance images of rat livers as described in Example III.
Figure 20:
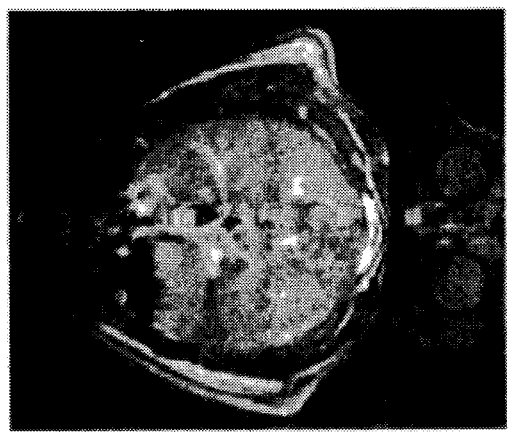
Figure 21:
Figure 22:
FIGS. 22–24 are magnetic resonance images of rat kidneys as described in Example III.
Figure 23:
Figure 24:

Representative magnetic resonance images of the rat liver and kidneys are shown in FIGS. 19–21 and 22–24, respectively: prior to administration shown in FIGS. 19 and 22; 5 minutes after administration shown in FIG. 20 and 23; and 60 minutes after admistration shown in FIGS. 21 and 24. The increase in T1-weighted signal intensity is readily apparent in both the liver and kidneys and has been found to persist throughout a 90 minute period.

Figure 25:
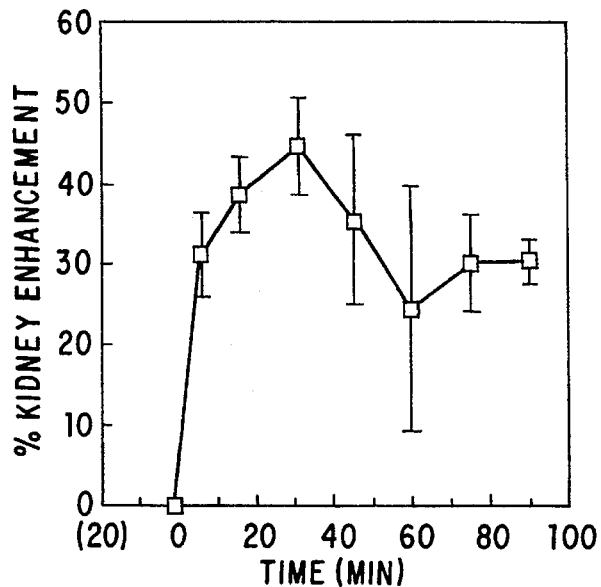
FIG. 25 is a graph showing average enhancement of magnetic resonance image intensity in rat kidneys versus time.
Figure 26:
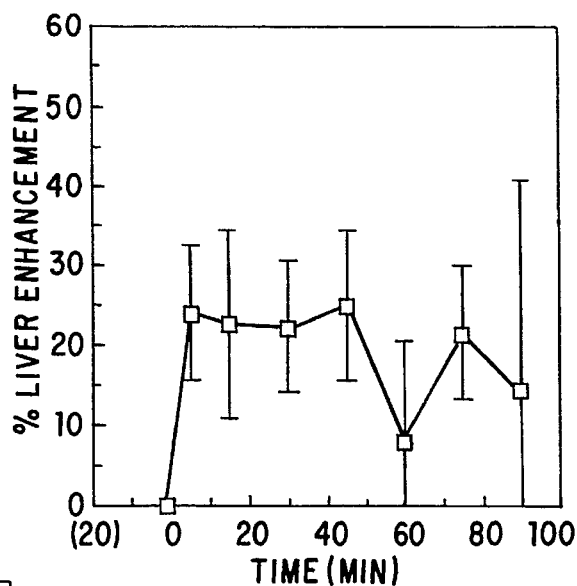
FIG. 26 is a graph showing average enhancement of magnetic resonance image intensity in rat livers versus time.
Figure 27:
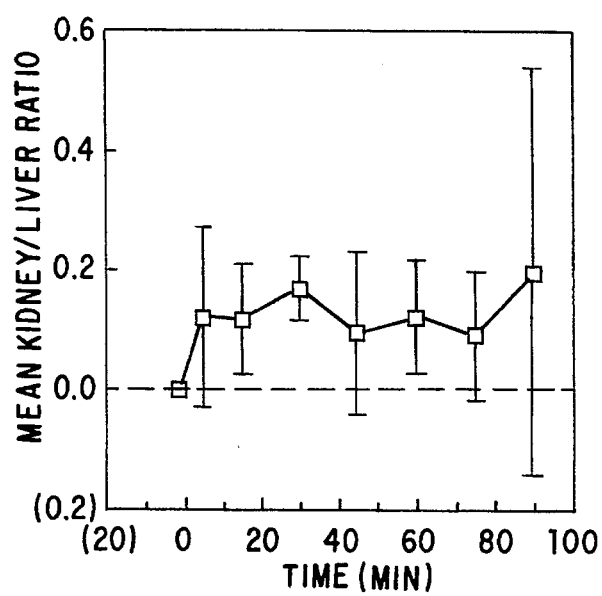
FIG. 27 is a graph showing the ratio of enhancement shown in FIGS. 25–26 of kidneys to liver, relative to precontrast enhancement versus time.

The average enhancement of magnetic resonance intensity for ROIs within the kidney and liver for all six experiments are shown in FIGS. 25 and 26, respectively. These data were not corrected for the intensity variation of the phantoms. The kidneys enhanced an average of 34% over 90 minutes, reaching a maximum of 45% enhancement at about 30 minutes. The liver enhanced an average of about 20% over 90 minutes, reaching a maximum of about 23% at about 5 to 40 minutes. FIG. 27 shows the ratio of enhancement, relative to precontrast enhancement, of the kidneys to liver, showing the time course of enhancement of these two organs to be similar, indicating that the enhancement agent was not selectively eliminated by either of these organs during the 90 minute experimental time period. This indicates recirculation of the enhancement agent in the blood pool of the rats.

This Example illustrates that the enhancement seen in the liver and kidneys, both highly vascularized organs, is easily visible even at a dose of 0.015 mmol $Gd^{+3}$/kg, one tenth the normal clinical dose of Gd-diethylenetriamine pentaacetic acid for magnetic resonance imaging. The high magnetic resonance sensitivity of the paramagnetic polymerized lipid preparation results from: (1) The particulate nature of the polymerized lipid slows the correlation time for reorientation of the $Gd^{+3}$ ion, which concentrates the power of the relaxation-effecting magnetic fluctuations in the regime of the water proton Larmor frequency and results in a higher molar relaxivity per $Gd^{+3}$ ion of 11.2 $mM^{-1}s^{-1}$,, as compared with Gd-diethylenetriamine pentaacetic acid of 4.2 $mM^{-1}s^{-1}$; and (2) The paramagnetic polymerizied lipid particles are confined to the blood pool and do not leak into the interstitial spaces, as does Gd-diethylenetriamanine pentaacetic acid. The reduced volume of distribution leads to a relatively increased blood pool concentration of gadolinium for the paramagnetic polymerized liposomes, as compared to a similar body weight dosage of Gd-diethylenetriamine pentaacetic acid.

Extended recirculation of the paramagnetic polymerized liposomes and their lack or absence of retention by the kidneys and liver is evident from the prolonged magnetic resonance intensity enhancement and the constant ratio of enhancement for these organs, as compared to Gd-diethylenetriamine pentaacetic acid, which is eliminated from the blood pool within a few minutes. The prolonged recirculation of the paramagnetic polymerized liposomes reults from reduction in phagocytosis by macrophages of the reticuloendothelial system by selection and control of the particle size and, perhaps, by use of polyethylene linkers for attachment of the $Gd^{+3}$ ion. Evasion of the reticuloendothelial system is probably complemented by evasion of the immune system by use of phosphatidyl choline, which is the major component of mammalian cells, as the matrix for presentation of the paramagnetic and ligand-bearing paramagnetic polymerized liposomes of this invention.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

We claim:

1. A polymerized liposome image contrast agent composition consisting essentially of: liposome forming lipids, said liposome forming lipids having active hydrophilic head groups selected from the group consisting of diethylenetriamine pentaacetic acid, ethylenedinitrile tetraacetic acid, tetraazacyclododecane 1,4,7,10-tetraacetic acid, and cyclohexane- 1,2,-diamino-N,N'-diacetate, said active hydrophilic head groups having functional surface groups chelated with an image contrast enhancement agent; said liposome forming lipids having hydrophobic tail groups polymerized with a hydrophobic tail group of an adjacent said liposome forming lipid through a functional group selected from the group consisting of diacetylene, olefin, acetylene nitrile, styrene, ester, thiol, amide, α, βunsaturated ketone, and α, βunsaturated aldehyde; said hydrophilic head groups and said hydrophobic tail groups linked to said liposome forming lipid by a variable length linker portion selected from the group consisting of variable length polyethylene glycol, polypropylene glycol and polyglycine.

2. A polymerized liposome image contrast agent composition according to claim 1 wherein said active hydrophilic head group is diethylenetriamine pentaacetic acid and said hydrophobic tail group is diacetylene.

3. A polymerized liposome image contrast agent composition according to claim 1 wherein said active head group is diethylenetriamine pentaacetic acid-bis(10,12-pentacosadiynoic amide) lanthanide ion chelator and said hydrophobic tail group is diacetylene.

4. A polymerized liposome image contrast agent composition according to claim 1 wherein said image contrast enhancement agent is selected from the group consisting of $Gd^{3+}$, $Dy^{3+}$, Tc and In 5. A polymerized liposome image contrast agent composition according to claim i wherein said hydrophilic head group comprises a lanthanide-diethylenetriamine pentaacetic acid chelate.

6. A polymerized liposome image contrast agent composition consisting essentially of: liposome forming lipids, said liposome forming lipids having active hydrophilic head groups selected from the group consisting of diethylenetriamine pentaacetic acid, ethylenedinitrile tetraacetic acid, tetraazacyclododecane 1,4,7,10-tetraacetic acid, and cyclohexane- 1,2,-diamino-N,N'-diacetate, a portion of said active hydrophilic head groups having functional surface groups chelated with an image contrast enhancement agent and additional said active hydrophilic head groups having attached targeting active agents; said liposome forming lipids having hydrophobic tail groups polymerized with a hydrophobic tail group of an adjacent said liposome forming lipid through a functional group selected from the group consisting of diacetylene, olefin, acetylene, nitrile, styrene, ester, thiol, amide, α, βunsaturated ketone, and α, β unsaturated aldehyde; said hydrophilic head groups and said hydrophobic tail groups linked to said liposome forming lipid by a variable length linker portion selected from the group consisting of variable length polyethylene glycol, polypropylene glycol and polyglycine.

7. A polymerized liposome image contrast agent composition according to claim 6 wherein said additional hydrophilic head groups are selected from the group consisting of biotin, amine, carboxylic acid and isothiocyanate.

8. A polymerized liposome contrast agent composition according to claim 6 wherein said targeting active agent is a ligand.

9. A polymerized liposome image contrast agent composition according to claim 6 wherein said image contrast enhancement agent is selected from the group consisting of $Gd^{3+}$, $Dy^{3+}$, Tc and In.

10. A polymerized liposome image contrast agent composition according to claim 6 wherein said hydrophilic head group comprises a lanthanide-diethylenetriamine pentaacetic acid chelate.

11. A polymerized liposome image contrast agent composition according to claim 6 wherein said active hydrophilic head group is diethylenetriamine pentaacetic acid and said hydrophobic tail group is diacetylene.

12. A polymerized liposome image contrast agent composition according to claim 6 wherein said active head group is diethylenetriamine pentaacetic acid-bis(10,12-pentacosadiynoic amide) lanthanide ion chelator and said hydrophobic tail group is diacetylene.

13. A polymerized liposome image contrast agent composition according to claim 6 wherein said targeting active agent is selected from the group consisting of protein, peptide and antibody.

14. A polymerized liposome image contrast agent composition according to claim 6 wherein said image contrast enhancement agent comprises metal chelated lipids in about 0 to about 30 percent for T1 molar relaxivity contrast agents and about 50 to about 99 percent for T2* molar relaxivity contrast agents.

* * * * *

UNITED STATES PATENT AND TRADEMARK OFFICE
CERTIFICATE OF CORRECTION

PATENT NO. : 5,512,294
DATED : 30 April 1996
INVENTOR(S) : King C. LI et al.

It is certified that error appears in the above—identified patent and that said Letters Patent is hereby corrected as shown below:

On title page, item [76]
Delete the name of the fifth inventor and in its place insert:

--Francois D. Tropper--

Signed and Sealed this

Fifth Day of November, 1996

Attest:

BRUCE LEHMAN

Attesting Officer   Commissioner of Patents and Trademarks